United States Patent
Francis et al.

(10) Patent No.: US 12,408,937 B2
(45) Date of Patent: Sep. 9, 2025

(54) TIP FOR A SURGICAL INSTRUMENT AND RELATED METHODS

(71) Applicant: Revolve Surgical Inc., Toronto (CA)

(72) Inventors: Peter Francis, London (CA); Peter Alexander Gordon, Toronto (CA)

(73) Assignee: Revolve Surgical Inc., Toronto (CA)

( * ) Notice: Subject to any disclaimer, the term of this patent is extended or adjusted under 35 U.S.C. 154(b) by 0 days.

(21) Appl. No.: 18/258,623

(22) PCT Filed: Dec. 19, 2021

(86) PCT No.: PCT/IB2021/061998
§ 371 (c)(1),
(2) Date: Sep. 14, 2023

(87) PCT Pub. No.: WO2022/137068
PCT Pub. Date: Jun. 30, 2022

(65) Prior Publication Data
US 2024/0050116 A1 Feb. 15, 2024

Related U.S. Application Data

(60) Provisional application No. 63/129,103, filed on Dec. 22, 2020.

(51) Int. Cl.
*A61B 17/29* (2006.01)
*A61B 34/00* (2016.01)
*A61B 34/30* (2016.01)

(52) U.S. Cl.
CPC .............. *A61B 17/29* (2013.01); *A61B 34/71* (2016.02); *A61B 2017/2927* (2013.01); *A61B 2017/2933* (2013.01); *A61B 2034/302* (2016.02)

(58) Field of Classification Search
CPC . A61B 17/29; A61B 34/71; A61B 2017/2927; A61B 2017/2933; A61B 2034/302
See application file for complete search history.

(56) References Cited

U.S. PATENT DOCUMENTS

| | | | |
|---|---|---|---|
| 7,066,926 B2 | 6/2006 | Wallace et al. | |
| 9,999,473 B2 | 6/2018 | Madhani et al. | |
| (Continued) | | | |

FOREIGN PATENT DOCUMENTS

| | | |
|---|---|---|
| EP | 2364825 A1 | 9/2011 |
| WO | 2014151952 A1 | 9/2014 |
| WO | 2016025134 A2 | 2/2016 |

OTHER PUBLICATIONS

Davinci Instrument & Accessory Catalog, Jan. 2019 (26 pages).
(Continued)

*Primary Examiner* — Brooke Labranche
(74) *Attorney, Agent, or Firm* — Aurora Consulting LLC; Albert Du; Ashley Sloat

(57) ABSTRACT

A tip for a surgical instrument comprising a cradle that is moveably mounted to a distal end of an elongate shaft. The cradle is rotatable relative to the elongate shaft about a pitch axis. A member is pivotally coupled to the cradle to move with and relative to the cradle about a grip axis that is substantially orthogonal to the pitch axis. The member is movable relative to the cradle about a yaw axis. In some embodiments, there is a second member that is pivotally coupled to the cradle to move with and relative to the cradle about a second grip axis that is substantially orthogonal to the pitch axis. In some embodiments, the first member and second member are selectably movable relative to each other between a closed configuration in which the first member contacts the second member and an open configuration.

21 Claims, 17 Drawing Sheets

(56) References Cited

U.S. PATENT DOCUMENTS

| | | | |
|---|---|---|---|
| 2006/0219065 A1* | 10/2006 | Jinno | A61B 34/70 |
| | | | 81/383 |
| 2008/0039256 A1 | 2/2008 | Jinno et al. | |
| 2012/0095451 A1 | 4/2012 | Hegeman et al. | |
| 2012/0220831 A1 | 8/2012 | Cooper et al. | |
| 2013/0110131 A1 | 5/2013 | Madhani et al. | |
| 2015/0366573 A1* | 12/2015 | Hähnle | A61B 17/00234 |
| | | | 606/205 |
| 2016/0303743 A1 | 10/2016 | Rockrohr | |

OTHER PUBLICATIONS

International Search Report dated Apr. 5, 2022 re PCT/IB2021/061998 (4 pages).

Jelinek et al. article titled "Classification of Joints Used in Steerable Instruments for Minimally Invasive Surgery—A Review of the State of the Art," Journal of Medical Devices, Copyright VC 2015 by ASME, Mar. 2015, vol. 9 / 010801-1, Downloaded From: http://medicaldevices.asmedigitalcollection.asme.org/ on Nov. 21, 2014 Terms of Use: http://asme.org/terms (12 pages).

Written Opinion dated Apr. 5, 2022 re PCT/IB2021/061998 (5 pages).

Extended European Search Report re 21909668.2-1113 / 4267012 PCT/IB2021061998 dated Sep. 30, 2024 (6 pages).

\* cited by examiner

TIP FOR A SURGICAL INSTRUMENT AND
RELATED METHODS

CROSS-REFERENCE TO RELATED APPLICATIONS

This application is a 35 U.S.C. 371 National Stage filing for PCT Application Ser. No. PCT/IB2021/061998, filed Dec. 19, 2021, which claims the priority benefit of U.S. Provisional Patent Application Ser. No. 63/129,103, filed Dec. 22, 2020, the contents of each of which are herein incorporated by reference in their entireties.

FIELD OF THE INVENTION

In one of its aspects, the present invention relates to a new design for an end-effector for a surgical instrument, and specifically to an end-effector that can achieve a range of different orientations.

BACKGROUND

Minimally Invasive Surgery (MIS) uses one or several small incisions in the abdominal wall of a patient to access an operation site. Surgical instruments are introduced through these incisions to provide a surgeon with visual feedback and tissue manipulation functionality. Ideally, these surgical instruments should include multiple degrees of freedom (DOF) and a slender or compact design to achieve maximum functionality in the operation site while minimizing damage to adjacent sites that are technically not in the surgical field. While many surgical instruments have been developed to fit at least some of these criteria, they still suffer from drawbacks, such as balancing compactness and articulation, joint articulation that requires larger sweeping motions, differential offsets for pitch and yaw axes for end-effector movement, axial or transverse splitting, axial spinning, reduced torsional stiffness, etc. Accordingly, there exists a need to develop new surgical instruments that include multiple degrees of freedom, especially in a compact design for use in MIS.

SUMMARY

One embodiment of the present disclosure is directed to a tip for an instrument. The tip includes: a first means for pivoting a first end-effector and a second end-effector about a pitch axis; a second means for rotating the first end-effector about a first grip axis that is orthogonal to the pitch axis; and a third means for rotating the second end-effector about a second grip axis that is orthogonal to the pitch axis.

In any of the preceding embodiments, the first means comprises one of: a cradle, a ball joint, a curved or arcuate structure slidably engaged with at least a portion of an end-effector, a pin joint, a sliding curved joint, or a rolling sliding joint.

In any of the preceding embodiments, the second means comprises one of: a first link member, a side-cradle, a curved or arcuate structure slidably engaged with at least a portion of an end-effector, or a pin and slot mechanism.

In any of the preceding embodiments, the third means comprises one of: a second link member, a side-cradle, a curved or arcuate structure slidably engaged with at least a portion of an end-effector, a pin and slot mechanism.

In any of the preceding embodiments, the tip further comprises a fourth means for rotating the tip about a shaft axis, wherein the tip is coupled to a distal end of a shaft of the surgical instrument.

In any of the preceding embodiments, the shaft axis is orthogonal to the pitch axis and the first and second grip axes.

In any of the preceding embodiments, the fourth means comprises an actuating apparatus configured to manipulate one or more of: the first means, the second means, the third means, or a combination thereof.

Another embodiment of the present disclosure is directed to a method of manipulating a tip of an instrument. The method includes: rotating a first end-effector about one of: a pitch axis, a first grip axis that is substantially orthogonal to the pitch axis, or a combination thereof; and rotating a second end-effector about one of: the pitch axis, a second grip axis that is substantially orthogonal to the pitch axis, or a combination thereof.

In any of the preceding embodiments, the second end-effector is rotatable about the second grip axis independently of the rotation of the first end-effector about the first grip axis. In any of the preceding embodiments, coordinated rotation of the first end-effector about the first grip axis and the second end-effector about the second grip axis causes the first end-effector and the second end-effector to move toward and away from each other between a closed configuration in which the first end-effector contacts the second end-effector and an open configuration in which the first end-effector is spaced apart from the second end-effector.

In any of the preceding embodiments, the pitch axis, the first grip axis, and the second grip axis all intersect each other at a common intersection point. In any of the preceding embodiments, the first grip axis and second grip axis are coaxial with each other and define a common yaw axis. In any of the preceding embodiments, the second end-effector is rotatable about the pitch axis independently of the rotation of the first end-effector about the pitch axis.

In any of the preceding embodiments, the first and/or second end-effector are one of: a member, a grasper, a sensorized end-effector, a force-torque sensor, a material removal tool, a collision sensor, a tool changer, a laser, a hook, a cautery/electrosurgery tip, a clip applier, a needle driver, a scissors, an ultrasonic energy instrument, an irrigation tip, a vessel sealer, a stapler, a base, a protrusion, or a base coupled to a protrusion.

Another embodiment of the present disclosure is directed to a tip for an instrument. The tip includes a cradle that is moveably mounted to a distal end of an elongate shaft and configured to rotate relative to the elongate shaft about a pitch axis; and a member pivotally coupled to the cradle and configured to move with the cradle about the pitch axis and to pivot relative to the cradle about a first grip axis.

In any of the preceding embodiments, the first grip axis is substantially orthogonal to the pitch axis.

In any of the preceding embodiments, the member is movable toward and away from a shaft axis of the elongate shaft about the yaw axis.

In any of the preceding embodiments, the tip further comprises a second member pivotally coupled to the cradle and configured to move with the cradle about the pitch axis and to pivot relative to the cradle about a second grip axis that is substantially orthogonal to the pitch axis.

In any of the preceding embodiments, the second member is movable relative to both the cradle and the member about the yaw axis.

In any of the preceding embodiments, the member and second member are selectably movable toward and away from each other between a closed configuration in which the member contacts the second member and an open configuration in which the member is spaced apart from the second member.

In any of the preceding embodiments, the tip further comprises an actuating apparatus that is configured to independently rotate the cradle about the pitch axis, and pivot the member about the grip axis.

In any of the preceding embodiments, the member is one of: an end-effector, a grasper, a sensorized end-effector, a force-torque sensor, a material removal tool, a collision sensor, a tool changer, a laser, a hook, a cautery/electrosurgery tip, a clip applier, a needle driver, a scissors, an ultrasonic energy instrument, an irrigation tip, a vessel sealer, a stapler, a base, a protrusion, or a base coupled to a protrusion.

In any of the preceding embodiments, the member is directly mounted on the cradle. In any of the preceding embodiments, the cradle comprises an arcuate body and a rail portion that is configured to slidingly engage with a first complementary bushing structure on the shaft.

In any of the preceding embodiments, the shaft comprises a second complementary bushing structure that is configured to slidingly engage the rail portion of the cradle.

In any of the preceding embodiments, the second complementary bushing structure is spaced apart from the first complementary bushing structure.

In any of the preceding embodiments, the first bushing structure is opposite from the second bushing structure.

In any of the preceding embodiments, the first grip axis and the second grip axis are coaxial with each other.

In any of the preceding embodiments, the member comprises a first base and the second member comprises a second base are connected to the cradle via a common pin joint.

In any of the preceding embodiments, the arcuate body of the cradle extends between a first cradle end and a second cradle end and defines a cradle angle that is between about 45 degrees and about 270 degrees. In any of the preceding embodiments, the cradle angle is about 180 degrees.

In any of the preceding embodiments, the tip further comprises an actuating apparatus that is configured to independently rotate the cradle about the pitch axis, pivot the member about the first grip axis, and pivot the second member about the second grip axis In any of the preceding embodiments, the actuating apparatus comprises a cradle cable extending axially through the shaft and being connectable to a cradle drive apparatus, the cradle cable being connected to the cradle whereby movement of the cradle cable through the shaft causes rotation of the cradle about the pitch axis.

In any of the preceding embodiments, the member or the first base and the second member or the second base are pivotally connected to the cradle using a hollow pivot pin such that the cradle cable is configured to pass through the hollow pivot pin.

In any of the preceding embodiments, a portion of the cradle cable within the hollow pivot pin is configured to extend along the first grip axis.

In any of the preceding embodiments, the tip further comprises a first linkage member having a first arcuate body portion that is rotatable about the pitch axis, relative to the shaft, and independently of the cradle.

In any of the preceding embodiments, the first linkage member is drivingly connected to the member so that pivoting of the first arcuate body portion about the pitch axis causes a corresponding pivoting of the member about the first grip axis.

In any of the preceding embodiments, the tip further comprises a second linkage member having a second arcuate body portion that is rotatable about the pitch axis, relative to the shaft, and independently of both the cradle and the first arcuate body portion.

In any of the preceding embodiments, the second linkage member is drivingly connected to the second member so that pivoting of the second arcuate body portion about the pitch axis causes a corresponding pivoting of the second member about the second grip axis.

In any of the preceding embodiments, the shaft further comprises a frame, such that one or more of: the first bushing structure, the second bushing structure, and the cradle cable are positioned in the frame.

Another embodiment of the present disclosure includes a tip for an instrument. The tip includes: a cradle that is moveably mounted to a distal end of an elongate shaft and configured to rotate relative to the elongate shaft about a pitch axis; a first member pivotally coupled to the cradle and configured to move with the cradle about the pitch axis and to pivot relative to the cradle about a first grip axis that is substantially orthogonal to the pitch axis; and a second member pivotally coupled to the cradle and configured to move with the cradle about the pitch axis and to pivot relative to the cradle about a second grip axis that is substantially orthogonal to the pitch axis.

In any of the preceding embodiments, the second member is movable relative to both the cradle and the first member about a yaw axis.

In any of the preceding embodiments, the first member and second member are selectably movable toward and away from each other between a closed configuration in which the first member contacts the second member and an open configuration in which the first member is spaced apart from the second member.

In any of the preceding embodiments, the tip further comprises an actuating apparatus that is configured to independently rotate the cradle about the pitch axis, pivot the first member about the first grip axis, and pivot the second member about the second grip axis.

In any of the preceding embodiments, the cradle comprises an arcuate body.

Another embodiment of the present disclosure is directed to a tip for an instrument. The tip includes: a frame extending along a frame axis between an outer frame end and an inner frame end and connectable to a distal end of an elongate shaft; a cradle that is moveably coupled to the frame, the cradle comprising an arcuate body that is rotatable relative to the frame about a pitch axis; a first gripping member having a first base and a first protrusion extending from the first base, the first base being pivotally coupled to the cradle to move with the cradle about the pitch axis and to pivot relative to the cradle about a first grip axis that is substantially orthogonal to the pitch axis; and a second gripping member having a second base and a second protrusion extending from the second base, the second base being pivotally coupled to the cradle to move with the cradle about the pitch axis and to pivot relative to the cradle about a second grip axis that is substantially orthogonal to the pitch axis.

In any of the preceding embodiments, the second gripping member is movable relative to both the cradle and the first gripping member about a yaw axis.

In any of the preceding embodiments, the first protrusion and second protrusion are selectably movable toward and away from each other between a closed configuration in which the first protrusion contacts the second protrusion and an open configuration in which the first protrusion is spaced apart from the second protrusion In any of the preceding embodiments, the frame axis intersects the pitch axis.

In any of the preceding embodiments, the frame axis intersects at least one of: the first grip axis and the second grip axis.

In any of the preceding embodiments, the frame axis, the pitch axis, the first grip axis, and the second grip axis all intersect each other at a common intersection point.

In any of the preceding embodiments, the common intersection point is axially outboard of the outer end of the frame.

In any of the preceding embodiments, the first grip axis and the second grip axis are coaxial with each other.

In any of the preceding embodiments, the first base and the second base are connected to the cradle via a common pin joint.

In any of the preceding embodiments, the arcuate body of the cradle extends between a first cradle end and a second cradle end and defines a cradle angle that is between about 45 degrees and about 270 degrees. In any of the preceding embodiments, the arcuate body of the cradle extends between a first cradle end and a second cradle end and defines an angular sweep of the arcuate body that is between about 45 degrees and about 270 degrees. In any of the preceding embodiments, the cradle angle or angular sweep is about 180 degrees.

In any of the preceding embodiments, the cradle is positionable in a neutral position in which the first cradle end and the second cradle end are disposed axially outboard of the outer frame end.

In any of the preceding embodiments, when the cradle is in the neutral position, a cradle plane extending between the first cradle end and the second cradle end is substantially orthogonal to the frame axis.

In any of the preceding embodiments, the cradle is rotatable in a first direction from the neutral position to a first limit position, in which the first cradle end is disposed axially outboard of the outer frame end and the second cradle end is disposed axially inboard of the outer frame end.

In any of the preceding embodiments, a maximum rotation of cradle between the neutral position and the first limit position is about 90 degrees.

In any of the preceding embodiments, the cradle plane is substantially parallel to the frame axis when the cradle is in the first limit position.

In any of the preceding embodiments, the cradle is rotatable in an opposing second direction from the neutral position to a second limit position, in which the second cradle end is disposed axially outboard of the outer frame end and the first cradle end is disposed axially inboard of the outer frame end.

In any of the preceding embodiments, a maximum rotation of cradle between the neutral position and the second limit position is about 90 degrees.

In any of the preceding embodiments, the cradle plane is substantially parallel to the frame axis when the cradle is in the second limit position.

In any of the preceding embodiments, the cradle is disposed within an axial cross-section of the frame when the cradle is in each of the neutral position, the first limit position, and the second limit position.

In any of the preceding embodiments, the cradle is disposed within a frame projection area when the cradle is in each of the neutral position, the first limit position, and the second limit position.

In any of the preceding embodiments, the cradle comprises a rail portion that slidingly engages with a first complementary arcuate groove on the frame.

In any of the preceding embodiments, the frame comprises a second complementary arcuate groove that engages the rail portion and is spaced apart from the first complementary arcuate groove.

In any of the preceding embodiments, the first arcuate groove is opposite from the second arcuate groove.

In any of the preceding embodiments, the cradle comprises a rail portion that slidingly engages with a first complementary bushing structure on the frame.

In any of the preceding embodiments, the frame comprises a second complementary bushing structure that engages the rail portion and is spaced apart from the first complementary bushing structure.

In any of the preceding embodiments, the first bushing structure is opposite from the second bushing structure.

In any of the preceding embodiments, the tip further comprises an actuating apparatus that is configured to independently rotate the cradle about the pitch axis, pivot the first gripping member about the first grip axis, and pivot the second gripping member about the second grip axis In any of the preceding embodiments, the actuating apparatus comprises a cradle cable extending axially through the frame and being connectable to a cradle drive apparatus, the cradle cable being connected to the cradle whereby movement of the cradle cable through the frame causes rotation of the cradle about the pitch axis.

In any of the preceding embodiments, the first base is pivotally connected to the cradle using a hollow pivot pin such that the cradle cable is configured to pass through the hollow pivot pin.

In any of the preceding embodiments, a portion of the cradle cable within the hollow pivot pin is configured to extend along the first grip axis.

In any of the preceding embodiments, the actuating apparatus further includes a cradle pulley that is disposed axially inboard from the outer end of the frame and is rotatable about a cradle pulley axis that is substantially parallel to the pitch axis, the cradle pulley being configured to guide the cradle cable and substantially maintain the cradle cable in close proximity to a curved outer surface of the cradle.

In any of the preceding embodiments, the tip further comprises a first linkage member having a first arcuate body portion that is rotatable about the pitch axis, relative to the frame, and independently of the cradle.

In any of the preceding embodiments, the first linkage member is drivingly connected to the first base so that pivoting of the first arcuate body portion about the pitch axis causes a corresponding pivoting of the first base about the first grip axis.

In any of the preceding embodiments, the tip further comprises a first linkage member having a first arcuate body portion that is rotatable about an axis parallel to the pitch axis, relative to the frame, and independently of the cradle.

In any of the preceding embodiments, the first linkage member is drivingly connected to the first base so that pivoting of the first arcuate body portion about the axis parallel to the pitch axis causes a corresponding pivoting of the first base about the first grip axis.

In any of the preceding embodiments, a pin projecting from the first arcuate link body is slidably received within a slot on the first base, and wherein the slot is configured so that contact between the pin and the slot, as the pin moves with the first arcuate body portion about the pitch axis, causes the corresponding pivoting of the first base about the first grip axis.

In any of the preceding embodiments, an arcuate rail on the first arcuate body portion is slidably received within an arcuate slot on the cradle, whereby the first arcuate linkage member is movably mounted to and at least partially supported by the first cradle.

In any of the preceding embodiments, an arcuate rail on the cradle is slidably received within an arcuate slot on the first arcuate body portion, whereby the first arcuate body portion is movably mounted to and at least partially supported by the cradle.

In any of the preceding embodiments, the tip further comprises a second linkage member having a second arcuate body portion that is rotatable about the pitch axis, relative to the frame, and independently of both the cradle and the first arcuate body portion.

In any of the preceding embodiments, the second linkage member is drivingly connected to the second base so that pivoting of the second arcuate body portion about the pitch axis causes a corresponding pivoting of the second base about the second grip axis.

In any of the preceding embodiments, the tip further comprises a second linkage member having a second arcuate body portion that is rotatable about an axis parallel to the pitch axis, relative to the frame, and independently of both the cradle and the first arcuate body portion.

In any of the preceding embodiments, the second linkage member is drivingly connected to the second base so that pivoting of the second arcuate body portion about the axis parallel to the pitch axis causes a corresponding pivoting of the second base about the second grip axis.

In any of the preceding embodiments, a pin projecting from the second arcuate body portion is slidably received within a slot on the second base, and wherein the slot is configured so that contact between the pin and the slot as the pin moves with the second arcuate body portion about the pitch axis causes the corresponding pivoting of the second base about the second grip axis.

In any of the preceding embodiments, an arcuate rail on the second arcuate body portion is slidably received within an arcuate slot on the cradle, whereby the second arcuate body portion is movably coupled to and at least partially supported by the cradle.

In any of the preceding embodiments, an arcuate rail on the cradle is slidably received within an arcuate slot on the second arcuate body portion, whereby the second arcuate body portion is movably coupled to and at least partially supported by the cradle.

In any of the preceding embodiments, the first arcuate body portion extends between a first body portion end and a second bod portion end and defines a first body portion angle that is between about 45 degrees and about 270 degrees. In any of the preceding embodiments, the first body portion angle is substantially the same as the cradle angle.

In any of the preceding embodiments, the first arcuate body portion extends between a first body portion end and a second body portion end and defines a first angular sweep of the first arcuate body portion that is between about 45 degrees and about 270 degrees.

In any of the preceding embodiments, the first angular sweep of the first arcuate body portion is substantially the same as the cradle angle.

In any of the preceding embodiments, the first arcuate body portion is positionable in a neutral position in which the first body portion end and the second body portion end are disposed axially outboard of the outer frame end.

In any of the preceding embodiments, when the first arcuate body portion is in the neutral position, a first body portion plane extending between the first body portion end and the second body portion end is substantially orthogonal to the frame axis and substantially parallel to the cradle plane.

In any of the preceding embodiments, the first arcuate body portion is rotatable relative to the frame, and independently of the cradle in a first direction from the neutral position to a first body portion limit position, in which the first body portion end is disposed axially outboard of the outer frame end and the second body portion end is disposed axially inboard of the outer frame end.

In any of the preceding embodiments, a maximum rotation between the neutral position and the first body portion limit position is about 90 degrees.

In any of the preceding embodiments, when the first arcuate body portion is in the first body portion limit position: the first body portion plane is substantially parallel to the frame axis; the first protrusion is spaced apart from the frame axis; and the first protrusion extends laterally beyond an outer edge of the frame.

In any of the preceding embodiments, when the first arcuate body portion is in the first body portion limit position: the first body portion plane is substantially parallel to the frame axis; the first protrusion is spaced apart from the frame axis; and the first protrusion extends outside of the frame projection area.

In any of the preceding embodiments, the first arcuate body portion is rotatable relative to the frame, and independently of the cradle in an opposing second direction from the neutral position to a second body portion limit position, in which the second body portion end is disposed axially outboard of the outer frame end and the first body portion end is disposed axially inboard of the outer frame end.

In any of the preceding embodiments, a maximum rotation between the neutral position and the second body portion limit position is about 90 degrees.

In any of the preceding embodiments, when the first arcuate body portion is in the second body portion limit position: the first body portion plane is substantially parallel to the frame axis; and the first protrusion is intersected by the frame axis.

In any of the preceding embodiments, the cradle is movable between the first limit position and the second limit position while the first arcuate body portion is in the first body portion limit position and when the first arcuate body portion is in the second body portion limit position.

In any of the preceding embodiments, the first arcuate body portion is disposed within an axial cross-section of the frame when the first arcuate body portion is in the each of the neutral position, the first body portion limit position, and the second body portion limit position.

In any of the preceding embodiments, the first arcuate body portion is disposed within a frame projection area when the first arcuate body portion is in the each of the neutral position, the first body portion limit position, and the second body portion limit position.

In any of the preceding embodiments, the first arcuate body portion comprises an arcuate frame rail portion that slidingly engages with a first complementary link groove on the frame.

In any of the preceding embodiments, the frame is connectable to the elongate shaft such that a rotation of the elongate shaft about a shaft axis causes rotation of the frame about the frame axis.

In any of the preceding embodiments, the frame is internally formed as an extension of the elongate shaft.

In any of the preceding embodiments, the frame has an outer diameter that is between about 3 mm and about 25 mm.

In any of the preceding embodiments, the frame has a substantially similar diameter as the elongate shaft.

In any of the preceding embodiments, the tip further comprises the elongate shaft.

BRIEF DESCRIPTION OF THE DRAWINGS

The foregoing is a summary, and thus, necessarily limited in detail. The above-mentioned aspects, as well as other aspects, features, and advantages of the present technology are described below in connection with various embodiments, with reference made to the accompanying drawings, wherein like reference numerals denote like parts, and in which.

DETAILED DESCRIPTION

Figure 1:
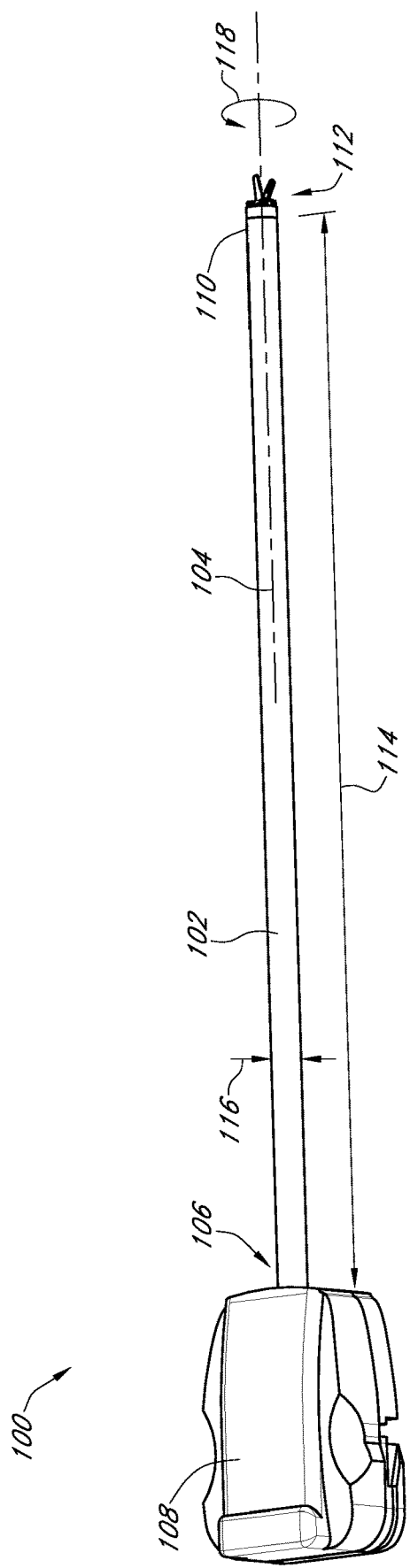
FIG. 1 is a perspective view of one example of a tip for a surgical instrument attached to an elongate shaft and an actuator module.

Various apparatuses or processes will be described below to provide an example of an embodiment of each claimed invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses described below. It is possible that an apparatus or process described below is not an embodiment of any claimed invention. Any invention disclosed in an apparatus or process described below that is not claimed in this document may be the subject matter of another protective instrument, for example, a continuing patent application, and the applicants, inventors, or owners do not intend to abandon, disclaim, or dedicate to the public any such invention by its disclosure in this document.

Surgeries in the abdominal region (such as general surgery, gynecological operations, urology operations, and the like) are typically performed with either an open method, where a large incision is made to access the surgical site, or a minimally invasive surgery (MIS) method, where multiple smaller incisions are made, and slender instruments are used to manipulate tissue at the surgical site. MIS, also known as keyhole or laparoscopic surgery, offers numerous advantages to the patient, such as decreased blood loss, reduced scarring and length of hospital stay. However, in many cases, the MIS approach is difficult to perform, and the open method is implemented instead. There are numerous challenges with MIS approaches, but the main difficulties stem from the limitations of the surgical instruments and lack of adequate visualization. The surgical instruments often lack dexterity, making it difficult to perform fine tasks, such as suturing, in highly confined spaces. One factor that can contribute to some of these challenges is the design of the tip of the surgical instrument that includes an end-effector, such as a gripper, that is intended to have multiple degrees of freedom. For example, the end-effector may be movable in roll, pitch and/or yaw axes and have some type of end-effector action (such as grasping or the like). Spinning of the instrument shaft itself can, in some designs, provide the roll for the tip, but the other types of movement need to be achieved by the tip design.

Instrument tips having these enhanced degrees of freedom can be referred to as wristed instruments, and two common types of such joints are described generally herein as pin-jointed and continuum apparatuses. These previous pin-joint designs usually combine movement about the yaw axis and end-effector movement by independently controlling each side of the grasper, while continuum designs may tend to have a separate mechanism for controlling the opening/closing of the graspers. While the pin-joint and continuum designs can be useful in some circumstances, these designs do have some shortcomings and there remains a need for improved tips for surgical devices. One example shortcoming posed by the existing pin-joint and continuum designs is that they are not particularly compact. When operating within small volumes such as the pelvis, it is important to be able to point instrument tips from separate surgical instruments directly toward each other via the wrist mechanism, and it is advantageous to require less space to achieve this configuration. The amount of space required is dependent on the compactness of the wrist mechanism. Additionally, less compact designs tend to lead to a relatively large "sweep" of the wrist/end-effector when changing the instrument's wrist orientation. This can be disadvantageous if the tip is positioned inside a patient as the sweeping of the end-effector may cause the tip to contact other tissue within the patient that is not the intended target of the surgeon/user. These cases may cause unwanted collisions between instruments or damage to surrounding tissue and/or may require a larger region that is cleared for access during a surgery than would be required with a more compact instrument tip. This continuum design may tend to suffer from this drawback more than the pin-joint design, but it can be a concern for both designs.

Another example of a shortcoming of the existing designs is that a change in orientation of the instrument may cause a relatively significant and unpredictable change in position in the tip/end-effector. For example, in some existing pin-jointed designs, the joint offsets for the pitch and yaw axes are different lengths and/or in series. This results in unpredictable changes in the tip/end-effector position when changing its orientation. The effect of this may be of relatively higher impact if the surgical tool is a hand operated or hybrid-type instrument design in which a human user is directly controlling the instrument's position. The impacts of this shortcoming can be somewhat reduced and possibly eliminated using relatively complicated and costly robotic surgical systems (as the system controller may be able to generally account for this type of position change). Accordingly, there remains a need for an improved surgical instrument tip that can address one or more of these shortcomings in the art and/or may provide other useful advantages.

The teachings in the present application may help to overcome at least some of the shortcomings in the art by providing a new tip for an instrument that is relatively compact and in which at least two of its degrees of freedom can be operated without undesired movement in the other degrees of freedom and/or without causing undue sweeping of the tip within the surgical area or causing unpredictable changes in a portion of the end-effector. In some examples described herein, the tip can be configured so that at least two and preferably all three of the axes defining its roll, yaw, and pitch degrees of freedom can intersect at a common point and that movement about at least two and preferably all three of the degrees of freedom can be done independently (or at least substantially/materially independently) of each other. This is also achieved in a design that is small enough to fit on the tip of an existing, hand operated or hybrid-operated surgical instrument and that is consistent with, and preferably slightly smaller, than the overall size of existing pin-joint and continuum tip designs. This can help enhance the usability of the tip in surgical applications.

The present teachings also include at least one example of how the instrument tip can be actuated/controlled, and preferably how the actuation mechanisms at the tip can be mostly (and in some cases preferably) mechanical in nature, such that electronics, motors, batteries, and the like are not required to be positioned in the instrument tip. This can help reduce costs and complexity of the tip design, which may help reduce the overall size of the tip. This may also help make the instrument relatively easier to clean and/or sterilize after it is used, such that the tip may be reused, if desired, without having to repair or replace batteries, electronics, or the like.

The various tip, wrist, and/or instrument features and designs described herein may be generally considered a controllable universal joint design.

In general, the tip described herein may improve upon existing designs at least for its compactness of articulation.

As used herein, compactness of articulation may comprise the volume that the tip requires to articulate through its range of motion. More compact articulation may be beneficial in procedures that require operating in a small volume, for example urologic al procedures (e.g., radical prostatectomy), gynecological procedures, neurosurgery, pediatrics, otolaryngology procedures. A less compact articulation may be beneficial in procedures that have a larger operating volume, for example procedures occurring in the abdominal cavity, chest cavity, etc., however compact articulation is also useful in procedures having a larger operating volume.

Although the tip described herein is described in the context of surgical applications, for example MIS, one of skill in the art will appreciate that the tip and related methods described herein may be used in maintenance, manipulation, assembly, applied robotics, manufacturing, machining, warehouse applications, etc., without departing from the scope of the present invention.

Further although, in an exemplary embodiment, a gripping member may be described, one of skill in the art will appreciate that the gripping member may comprise a member, a member or an end-effector that is pivotally coupled to a first means (e.g., cradle) for movement about the pitch axis, an end-effector, a grasper, a sensorized end-effector, a force-torque sensor, a material removal tool (e.g., cutting, drilling, deburring, etc.), a welding torch, a collision sensor, a tool changer, a laser, a hook, a cautery/electrosurgery tip, a clip applier, a needle driver, a scissors, an ultrasonic energy instrument, an irrigation tip, a vessel sealer, a stapler, etc. without departing from the scope of the present invention.

Still further, although two gripping members are shown in an exemplary embodiment, one of skill in the art will appreciate that there may be only one, more than one, a plurality, more than two, three, etc. end-effectors that form part of the tip design described herein, without departing from the scope of the present invention.

As used herein, "inboard" means or may include that a first component does not extend beyond or outside of another component or is projected inward. As used herein, "outboard" mean or may include that a first component at least partially extends beyond or at least partially outside of another component or is projected outward but remains within a projection of the other component. As a non-limiting example of inboard and outboard: if a hollow cylinder had a flat capped end, then a component that is outboard of the cylinder means outward from the flat capped end but within an extended cylinder projected in that direction. In contrast, a component that is inboard of the cylinder means within the cylinder.

In general, a tip for an instrument may include: a first means for rotating a member about a pitch axis; and a second means for rotating the member about a first grip axis that is orthogonal to the pitch axis.

In general, a tip for an instrument may include: a first means for rotating a member about a pitch axis; a second means for rotating a first portion of the member about a first grip axis that is orthogonal to the pitch axis; and a third means for rotating a second portion of the member about a second grip axis that is orthogonal to the pitch axis.

In general, a tip for an instrument may include: a first means for rotating a member and a second member about a pitch axis; a second means for rotating the first member about a first grip axis that is orthogonal to the pitch axis; and a third means for rotating the second member about a second grip axis that is orthogonal to the pitch axis.

In general, a first means may include one of: a cradle, a ball joint, a curved or arcuate structure slidably engaged with at least a portion of an end-effector, a pin joint, a sliding curved joint, a rolling sliding joint, etc. In general, a second means may include one of: a first link member, a side-cradle, a curved or arcuate structure slidably engaged with at least a portion of an end-effector, a pin and slot mechanism (e.g., pin or slot may be on at least a portion of the end-effector), etc. In general, a third means may include one of: a second link member, a side-cradle, a curved or arcuate structure slidably engaged with at least a portion of an end-effector, a pin and slot mechanism (e.g., pin or slot may be on at least a portion of the end-effector), etc.

In general, any of the tips described herein may include a fourth means for rotating the tip about a shaft axis, such that the tip is coupled to a distal end of a shaft of the instrument. In the embodiments described herein, the shaft axis is orthogonal to the pitch axis and the first and second grip axes, for example, when a pitch axis is in a neutral position or when the first and second grip axes (yaw axis) are in a neutral position.

In general, the fourth means may include a manual, partially automatic, automatic, robotic, purely mechanical, electro-mechanical, etc. actuating apparatus configured to manipulate one or more of: the first means, the second means, the third means, or a combination thereof.

In general, a tip for an instrument may include a cradle that is moveably coupled to a distal end of an elongate shaft and configured to rotate relative to the elongate shaft about a pitch axis; and an end-effector pivotally coupled to the cradle and configured to move with the cradle about the pitch axis and to pivot relative to the cradle about a first grip axis that is substantially orthogonal to the pitch axis, such that the end-effector is movable relative to the cradle about a yaw axis.

In general, the end-effector may be movable toward and away from a shaft axis of the elongate shaft about the yaw axis.

In general, a tip for an instrument may include a second end-effector pivotally coupled to the cradle and configured to move with the cradle about the pitch axis and to pivot relative to the cradle about a second grip axis that is substantially orthogonal to the pitch axis.

In general, the second end-effector may be movable relative to both the cradle and the first end-effector about the yaw axis.

In general, the end-effector and second end-effector may be selectably movable toward and away from each other between a closed configuration in which the end-effector contacts the second end-effector and an open configuration in which the end-effector is spaced apart from the second end-effector.

In general, a tip for an instrument may further include an actuating apparatus (manual, partially automatic, automatic, robotic, etc.) that is configured to independently rotate the cradle about the pitch axis, and pivot one or both of: the end-effector about the grip axis or the second end-effector about the second grip axis.

In general, a tip for an instrument may include a cradle that is moveably coupled to a distal end of an elongate shaft and configured to rotate relative to the elongate shaft about a pitch axis; a first end-effector pivotally coupled to the cradle and configured to move with the cradle about the pitch axis and to pivot relative to the cradle about a first grip axis that is substantially orthogonal to the pitch axis, such that the first end-effector is movable relative to the cradle about a yaw axis; and a second end-effector pivotally coupled to the cradle and configured to move with the cradle about the pitch axis and to pivot relative to the cradle about a second grip axis that is substantially orthogonal to the pitch axis.

In general, the second end-effector may be movable relative to both the cradle and the first end-effector about the yaw axis. In general, the first end-effector and second end-effector may be selectably movable toward and away from each other between a closed configuration in which the first end-effector contacts the second end-effector and an open configuration in which the first end-effector is spaced apart from the second end-effector.

In general, a tip for an instrument may include an actuating apparatus (manual, partially automatic, automatic, robotic, etc.) that is configured to independently rotate the cradle about the pitch axis, pivot the first end-effector about the first grip axis, and pivot the second end-effector about the second grip axis.

In general, the cradle and/or link members may comprise an arcuate body, although other shapes are also contemplated herein, such as arched, bent, bowed, curved, rounded, arciformed, etc.

In general, a method of manipulating a tip of an instrument includes: rotating a first end-effector about one of: a pitch axis, a first grip axis that is substantially orthogonal to the pitch axis, or a combination thereof; and rotating a second end-effector about one of: the pitch axis, a second grip axis that is substantially orthogonal to the pitch axis, or a combination thereof. The method may be performed by an actuating apparatus electrically and/or communicatively coupled to a processor or by a user with or without an actuating apparatus.

In general, the second end-effector may be rotatable about the second grip axis independently of the rotation of the first end-effector about the first grip axis.

In general, coordinated rotation of the first end-effector about the first grip axis and the second end-effector about the second grip axis causes the first end-effector and the second end-effector to move toward and away from each other between a closed configuration in which the first end-effector contacts the second end-effector and an open configuration in which the first end-effector is spaced apart from the second end-effector.

In general, the pitch axis, the first grip axis, and the second grip axis may all intersect each other at a common intersection point.

In general, the first grip axis and second grip axis may be coaxial with each other and define a common yaw axis.

In general, the second end-effector may be rotatable about the pitch axis independently of the rotation of the first end-effector about the pitch axis.

In general, the method may be a surgical method, a minimally invasive surgical method, a manufacturing method, a robotics-based method, a welding method, a logistics method, a method of using a tip to repair an object, etc. without departing from the scope of the present disclosure.

Potential general features of the system are described above and now an exemplary embodiment is described herein below, with reference to the drawings. The below described exemplary embodiment should not be seen as limiting the above possible generalities of the invention described above.

Figure 2:
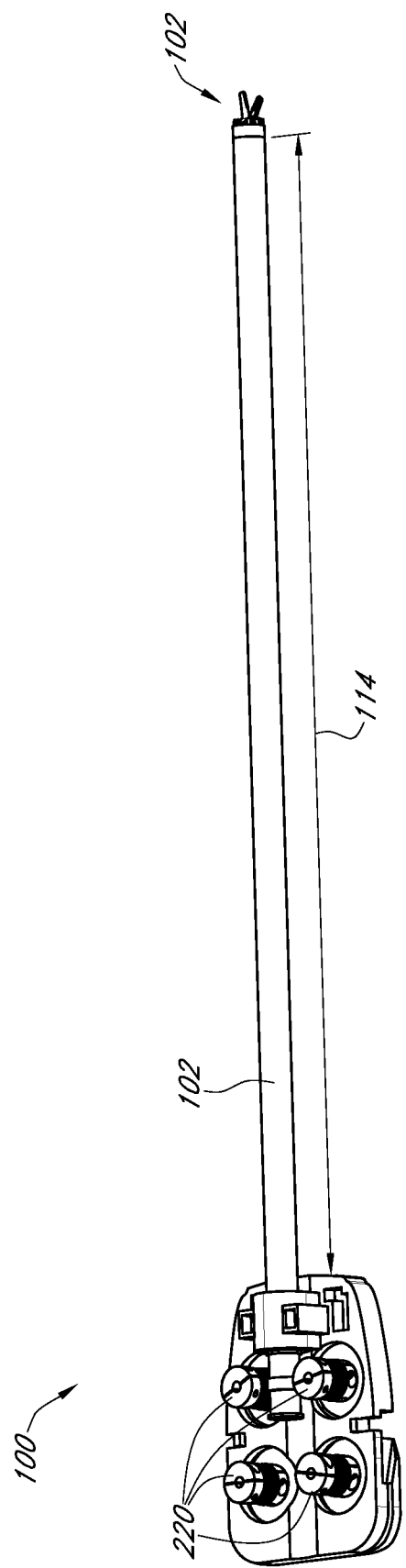
FIG. 2 is the perspective view of FIG. 1 showing the interior of the actuator module.

Referring to FIGS. 1 and 2, one example of a surgical instrument 100 includes an elongate shaft 102 that extends along a shaft axis 104. The shaft 102 has a first or proximal end 106 that is connected to a base or control portion of the instrument which, in this example, includes a drive apparatus 108 that can be used to help drive/actuate portions of the instrument, as described herein. The drive apparatus 108 may be a powered/robotic type apparatus and/or may alternatively include a manually actuated grip portion, handle or other suitable structure that is capable of providing the desired engagement with the actuating apparatus and cables described herein. Axially spaced from the proximal end 106 of the shaft 102, by a shaft length 114, is a second or distal end 110 that includes a tip 112.

The shaft length 114 can be any suitable length for use in surgery with a human or animal patient, and may be between about 10 cm and about 80 cm. The shaft 102 also defines a shaft diameter 116 that can be any suitable diameter for use in surgery with a human or animal patient, and may be between about 5 mm and about 15 mm, and preferably can be about between about 8 mm and about 10 mm and in some examples may be about 8 mm. In the illustrated example, the diameter 116 is substantially constant along the length 114 of the shaft 102, but in other surgical instrument designs, the shaft 102 can have different diameters along its length 114. The shaft 102 can be cylindrical as shown or may have a different shape, for example elliptical. As used herein to describe the diameter of the shaft, frame, etc., the diameter is measured at a cross-section of the shaft or frame that is perpendicular to a longitudinal or axial axis of the shaft or frame.

Preferably, the instrument 100 is configured such that the shaft 102 can be rotated about the shaft axis 104, as shown by arrows 118 in FIG. 1. The tip 112 that is mounted to the shaft 102 will also then rotate about the shaft axis 104 in a first degree of freedom that is referred to as a roll motion herein, such that the shaft axis 104 defines a roll axis 104. Optionally, the shaft 102 can be rotatably connected to its drive apparatus to provide the desired roll, or as shown in this example both the shaft 102 and drive apparatus 108 can be rotated together about the roll axis 104, either manually or using a supporting/stabilizing apparatus (not shown, but one example of a suitable apparatus is shown in PCT application no. PCT/CA2020/051237 entitled "A Hybrid, Direct-Control And Robotic-Assisted Surgical System", the contents of which are herein incorporated by reference in their entirety).

Referring to FIGS. 3-10, the illustrated example of the tip 112 includes a frame 120 that is attached to the distal end 110 of the shaft 102 and that extends along a respective frame axis 124. The frame axis 124 is preferably at least substantially parallel to the shaft axis 104 and in this example is at least substantially co-axial with the shaft axis 104. In this arrangement, rotation of the shaft 102 about the shaft axis 104 causes a corresponding rotation of the frame 120 about the frame axis 124. While shown as separate parts in this example, optionally some or all of the frame 120 and its features may be integrally formed with the shaft 102, such that some embodiments do not include a frame or the frame forms part of the shaft (being collectively then called a shaft). In other embodiments, for example including a frame, the frame may be independently rotatable from the shaft to achieve tip rotation.

The frame 120 is preferably shaped to have the same, or at least a substantially complementary shape to that of the shaft 102, and in this example has the same outer shape, and an outer surface 125 of the frame 120 remains exposed and forms part of the outer surface of the instrument 100. This arrangement has a frame diameter 122 (FIG. 4) that is between about 3 mm and about 25 mm and preferably, as shown, is the same as the shaft diameter 116. Alternatively, the frame diameter 122 may be greater than or less than the shaft diameter 116. Additionally, in some embodiments, a shorter frame length may be coupled to a longer shaft length and a longer frame length may be coupled to a shorter shaft length, so that the device can function for its intended purpose and accommodate one or more actuation mechanisms (e.g., pulleys, cables, etc.).

Figure 10:
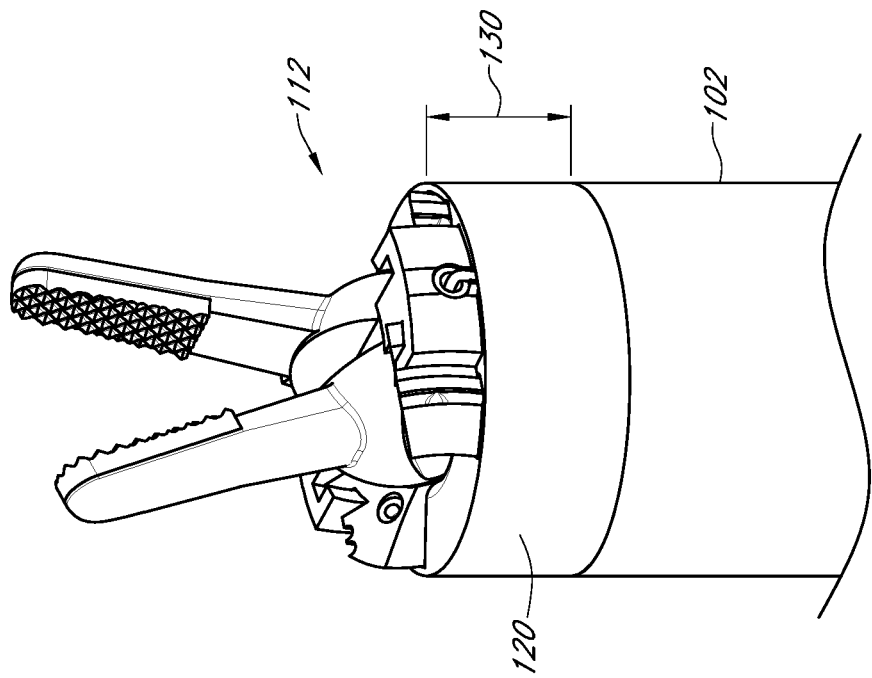
FIG. 10 is a perspective view of a frame combined with the components of FIG. 9.

In this example, the frame 120 defines an inner or proximal end 128 that is adjacent the shaft 102 and an outer or distal end 126 that is spaced from the inner end 128 along the frame axis 124 by a frame length 130 (as shown in FIG. 10). The frame length 130 can be any suitable length that can support and accommodate the tip features described herein, and may be between about 2 mm and about 30 mm, and preferably may be about 10 mm. An axial projection of the cross-sectional area of the frame 120, taken in a plane that is orthogonal to frame axis 124, beyond the outer end 126 of the frame 120, is referred to as a frame projection area and, in this example, is a generally cylindrical volume that is illustrated by the hatched region 138 in FIG. 4.

Figure 4:
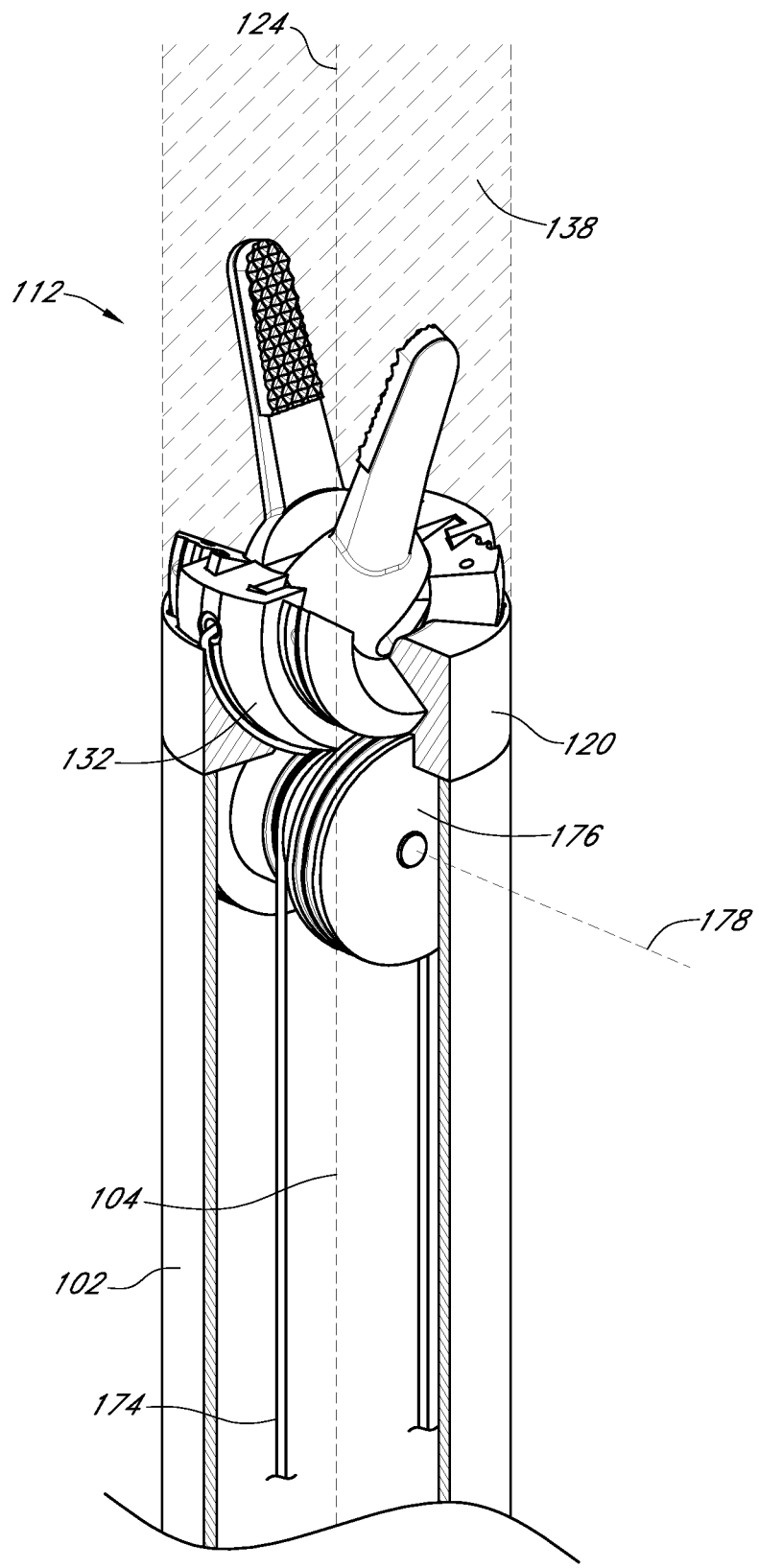
FIG. 4 is another perspective view of the tip for a surgical instrument of FIG. 3 with a portion of the frame and shaft cut-away.
Figure 6:
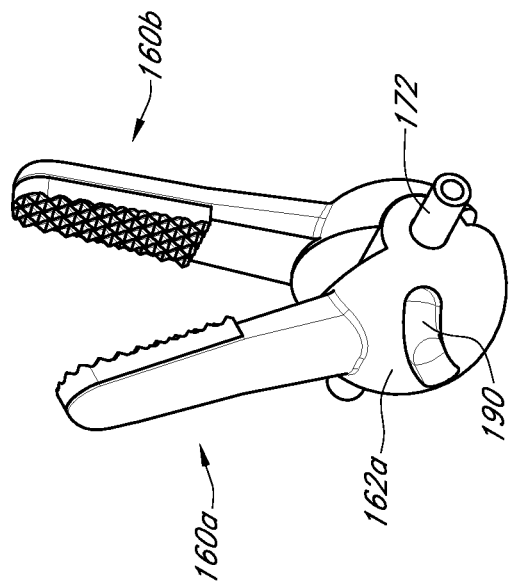
FIG. 6 is a perspective view of a first and second protrusion and respective base of a tip for a surgical instrument, each pivotable about a pin.
Figure 7:
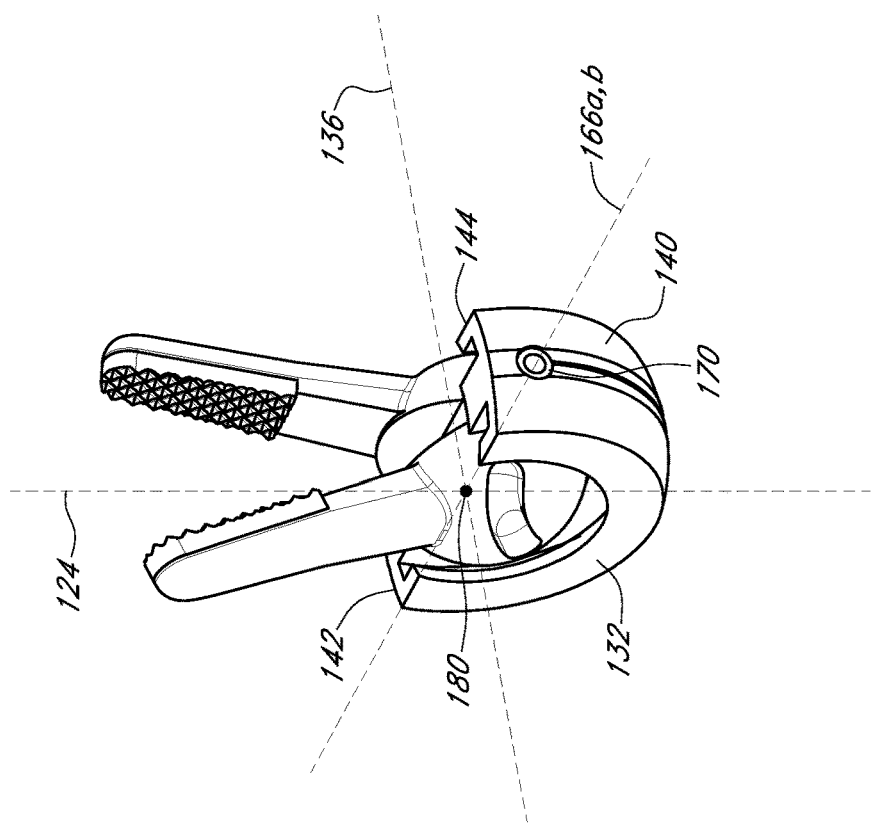
FIG. 7 is a perspective view of a cradle combined with the components of FIG. 6.
Figure 11:
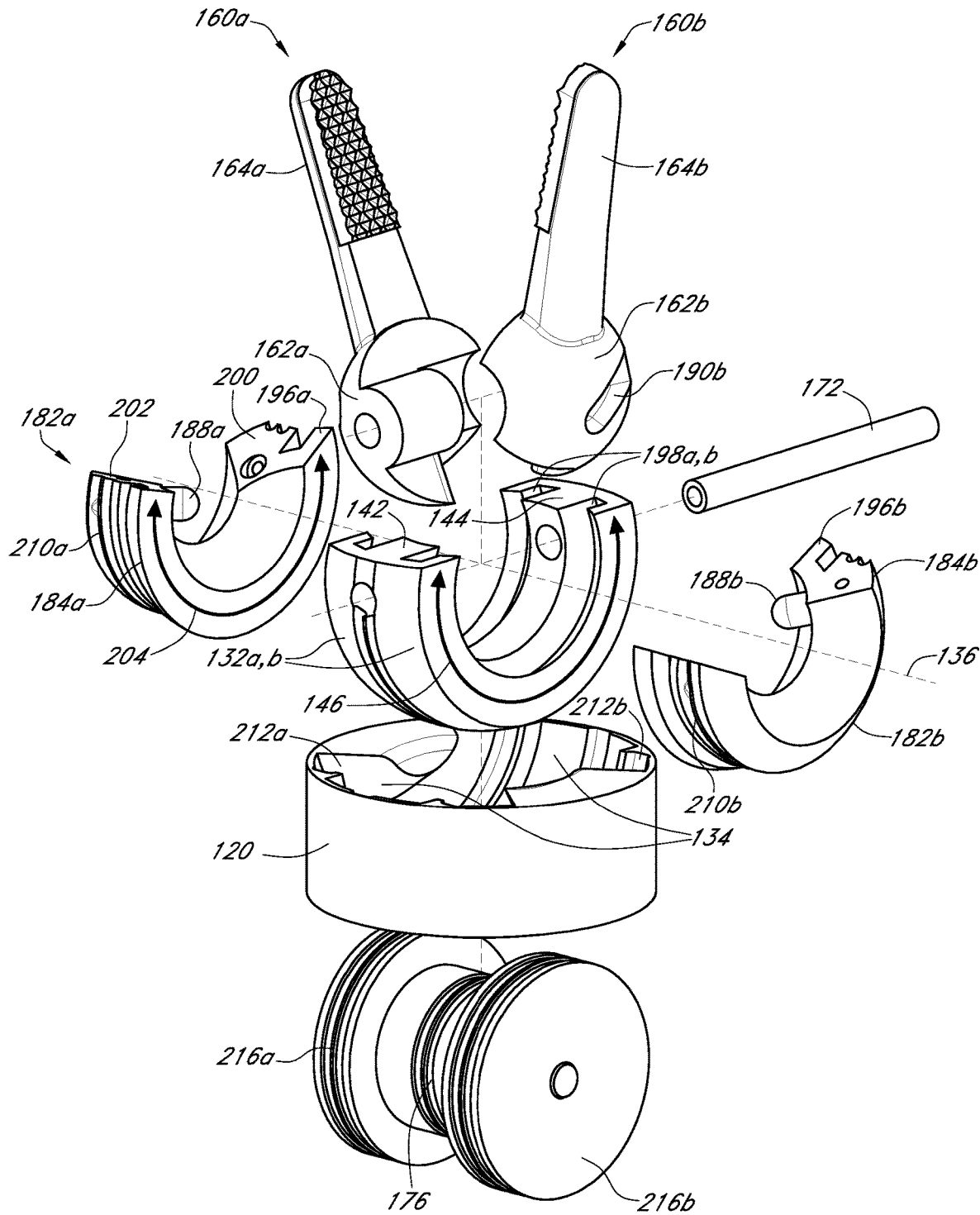
FIG. 11 is an exploded view of the surgical tip of FIG. 1

Referring to FIGS. 4 and 7, this example of the tip 112 includes a cradle 132 that is coupled to the frame 120 or directly to the shaft (with or without the frame) so that the cradle 132 can move relative to the frame 120 to provide a second degree of freedom for the tip 112. In the illustrated example, the cradle 132 includes a curved/arcuate body portion having a rail portion 140 on its outer surface that is complementary to and slides within a corresponding arcuate groove or bushing structure 134 (as shown in FIG. 11). Bushing structures 134 are spaced apart from each other on opposing sides of the frame 120 or shaft. In this arrangement, the cradle 132 slides along an arcuate path relative to the frame 120 (defined by the bushing structures 134) such the cradle 132 moves/pivots about a second axis which, in this example, is referred to as pitch axis 136.

Figure 3:
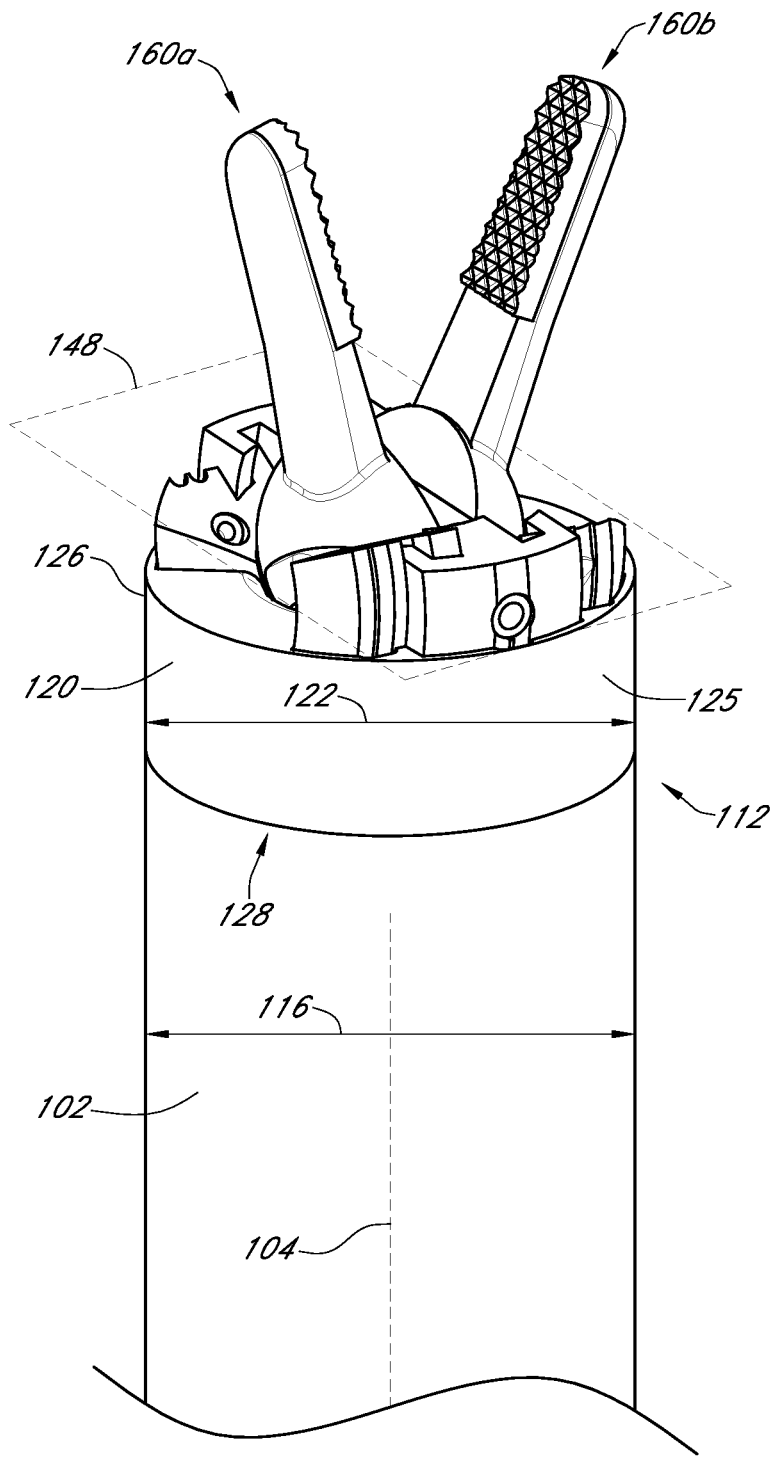
FIG. 3 is another perspective view of a tip for a surgical instrument.
Figure 18:
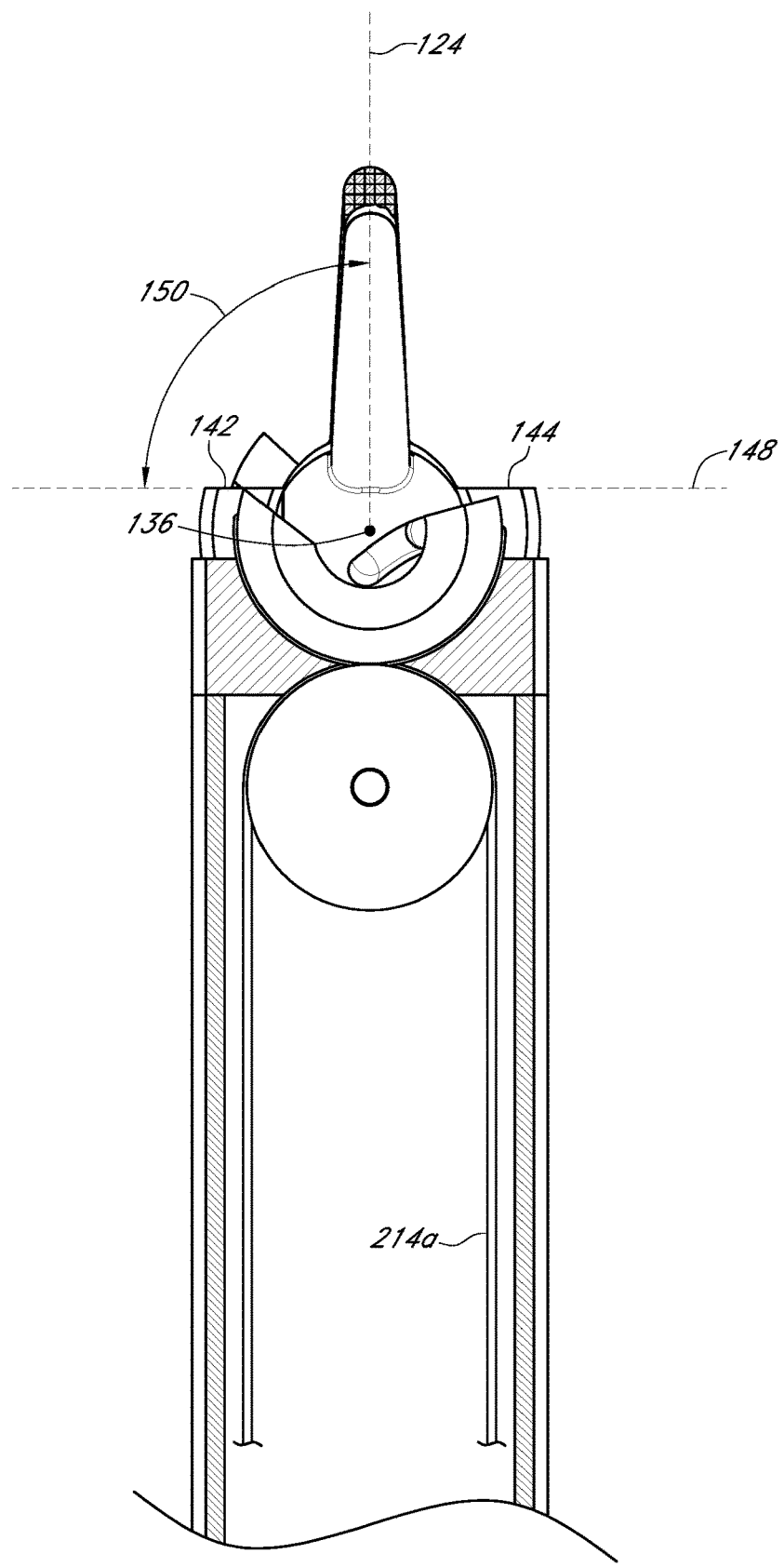
FIG. 18 is a side view of the surgical tip with a portion of the frame and elongate shaft removed.

As shown in FIG. 7, the arcuate body of the cradle 132 extends between a first end 142 and a second end 144, each of which have, in the present example, generally planar end surfaces, but may also comprise an angled surface (e.g., angled towards bodies 162*a,b*) to enable further movement of bodies 162*a,b* and protrusions 160*a,b*. The span of the cradle 132 between the ends 142 and 144 can define a cradle angle 146 (as shown by arrow 146 in FIG. 11) that is the angular sweep of cradle body 132. The cradle angle 146 may be any desired angle, with different angles giving different ranges of motion for the tip. For example, the cradle angle 146 may be between about 45 degrees and about 270 degrees and preferably, as shown in this example, may be about 180 degrees. In this configuration, a virtual cradle plane 148 (as shown in FIGS. 3 and 18) can be defined as the plane in which the cradle ends 142, 144 lie. Virtual cradle plane 148 is referenced herein to help describe the orientation of the cradle 132 relative to the frame 120 and other components.

For example, the cradle 132 can be pivoted relative to the frame 120 or shaft, about the pitch axis 136 (as shown, e.g., in FIGS. 7, 11) into a variety of different orientations. Referring to FIGS. 3 and 18, the cradle 132 can be positioned in a home or neutral position in which the first cradle end 142 and the second cradle end 144 are each disposed axially outboard of the outer end of the frame 120 or shaft and in which the cradle plane 148 is substantially orthogonal or perpendicular to the frame axis 124 or shaft axis, such that the cradle reference angle 150 (as shown in FIG. 18) is about 90 degrees. In this example, the cradle plane 148 is generally parallel to the pitch axis 136, perpendicular to the frame axis 124 or shaft axis, and is axially outboard from the pitch axis 136. From this neutral position, the cradle 132 can be rotated about the pitch axis 136 between opposed limit or maximum rotation pitch positions, the extent of which can be determined by the geometry of a given example of the frame 120 or shaft and cradle 132.

Figure 12:
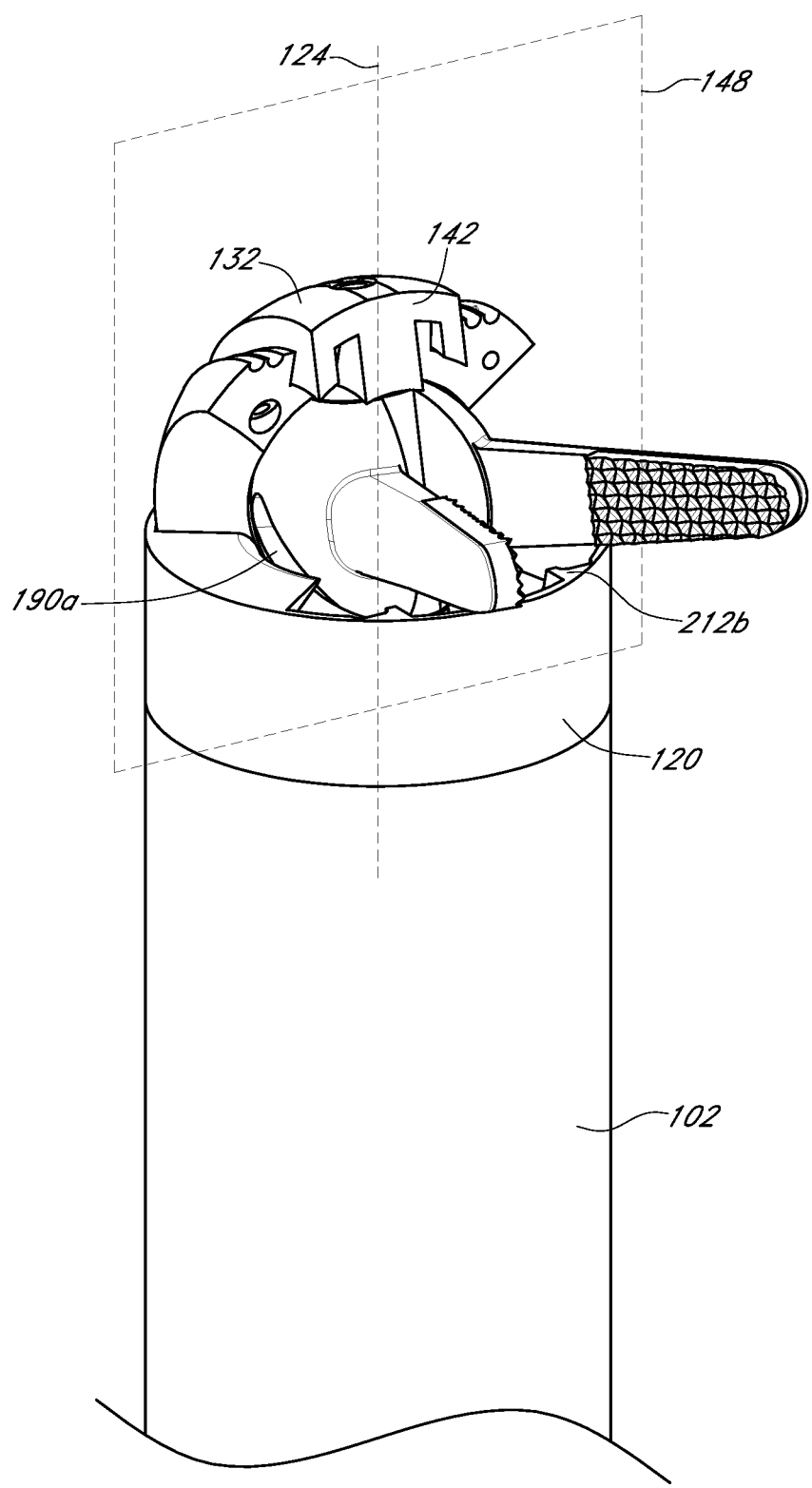
FIG. 12 is a perspective view of the surgical tip of FIG. 1 in a first pitch position.

Referring to FIG. 12, the cradle 132 is shown rotated from the neutral position, about a pitch axis 136, in a first direction to a first limit position (and may proceed through one or more intermediate position). In this example, when the cradle 132 is moved to the first limit position, the first cradle end 142 is disposed axially outboard of the outer or distal frame end (or distal shaft end), along the frame axis 124 or shaft axis, and the second cradle end 144 is disposed axially inboard of the outer or distal frame end or distal shaft end. This can be described as about 90 degree rotation from the neutral/home position of FIG. 3. Also, in this example, when the cradle 132 is in the first limit position, the cradle plane 148 is substantially parallel to the frame axis 124 or shaft axis, but may also be inclined relative to the frame axis 124 or shaft axis in other examples. One of skill in the art will appreciate that while a neutral position and a first limit position are described, there may exist an infinite number of positions between the neutral position and the first limit position, for example intermediate positions.

Similarly, the cradle 132 can be rotated in the opposite direction about the pitch axis 136 from the neutral position to a second limit position (and may proceed through one or more intermediate positions), in which the second cradle end 144 is disposed axially outboard of the outer or distal frame end (or distal shaft end) and the first cradle end 142 is disposed axially inboard of the outer or distal frame end (or shaft distal end). This can be described as about 90 degree rotation from the neutral/home position of FIG. 3 in the opposite direction as FIG. 12. Also, in this example when the cradle 132 is in the second limit position, the cradle plane 148 is substantially parallel to the frame axis 124 or shaft axis, but may also be inclined relative to the frame axis 124 or shaft axis in other examples. One of skill in the art will appreciate that while a neutral position and a second limit position are described, there may exist an infinite number of positions between the neutral position and the second limit position, for example intermediate positions.

Because of the design of the frame 120 and the cradle 132 in the figures shown herein, the cradle 132 remains entirely with or does not extend beyond or outside of the projected frame area 138 (shown in FIG. 4) throughout its entire range of motion, for example when the cradle 132 is in each of the home/neutral position, the first limit position, and the second limit position. This can help reduce the overall size of the tip 102. This may also help reduce or eliminate interference between the cradle 132 and objects that are beside or surrounding the shaft 104 and/or frame 120. Alternatively, in some examples the cradle may protrude laterally outside or beyond of the projected frame area 138.

To provide a desired gripping or grasping functionality for the tip 102, the present example includes a grasping mechanism that includes a first gripping member 160a and a complementary second gripping member 160b. The gripping members 160a,b in this example have analogous features, but in other examples may have different features or configurations.

Referring to FIGS. 5-11, in this example, each gripping member 160a,b has a respective base 162a,b and a respective protrusion portion 164a,b that extends from the base. As described elsewhere herein, a "base" and a "protrusion" may be used interchangeably with end-effector or member. Ultimately, a member or an end-effector or similar term is used to describe a component that is pivotally coupled to the cradle for movement about the pitch axis. The protrusion portions 164a,b can include a textured contact region, a tissue cutting region, a sensorized region, an electrocautery region, or other suitable design features, as described elsewhere herein, to allow them to grip, cut, or otherwise manipulate tissue and other substances. In some embodiments, a length from a base to a tip or end (opposite the base) of a gripping member may be about 10 cm to about 60 cm. Shorter distances in this range may minimize stroke length and increase collision potential with adjacent surgical instruments but provide additional control of movement during use. Longer distances in this range may increase stroke length and reduce collision potential. Specialties that may benefit from a shorter distance from base to tip may be, for example, transoral procedures, nasal procedures, or pediatric based procedures while specialties that may benefit from a longer distance from base to tip may be, for example, bariatric procedures.

Figure 14:
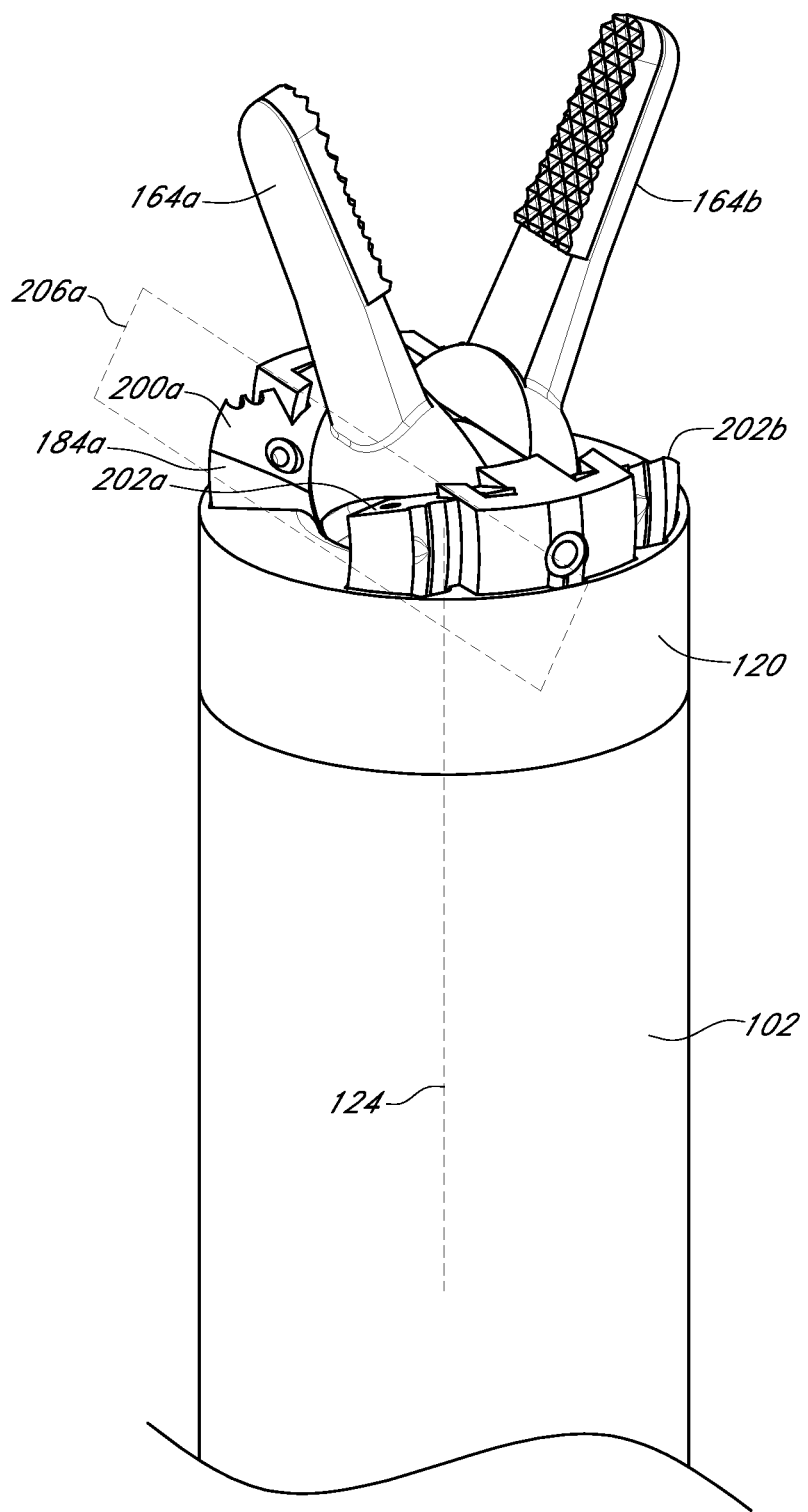
FIG. 14 is a perspective view of the surgical tip of FIG. 1 in an open configuration.
Figure 15:
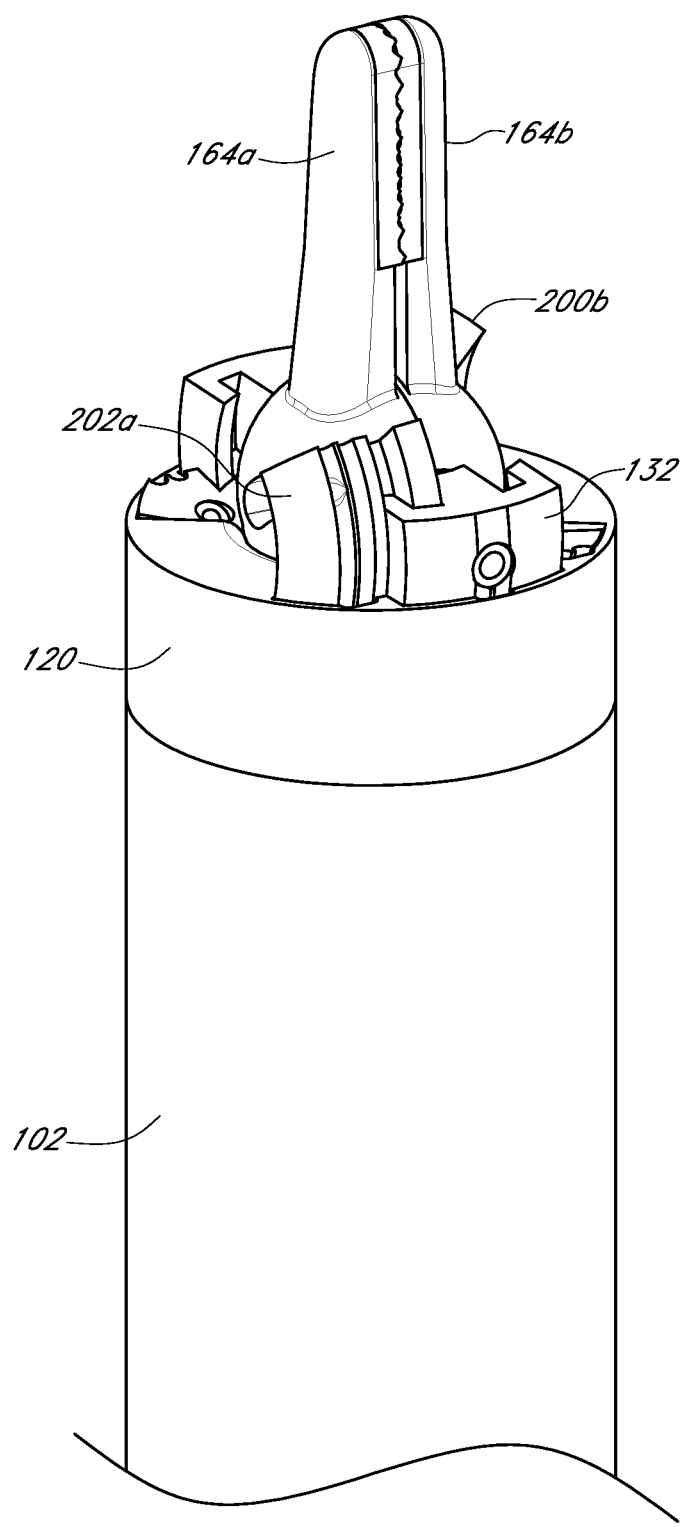
FIG. 15 is a perspective view of the surgical tip of FIG. 1 in a closed configuration.

The bases 162a,b are coupled to the cradle 132 such that they will move with the cradle 132 as it pivots about the pitch axis 136. In some embodiments, coupling comprises directly mounting a member or base or end-effector or like component to the cradle; in other embodiments, coupling comprises indirectly mounting (through one or more intermediate components) a member or base or end-effector or like components to the cradle. The bases 162a,b are also movable relative to the cradle 132 such that each gripping member 160a,b can pivot relative to the cradle 132 about respective gripping member or yaw axes 166a,b. The yaw axes 166a,b are preferably parallel to each other and substantially orthogonal to the pitch axis 124, and in the illustrated example, the yaw axes 166a,b are actually coaxial with each other (but could be spaced apart in other examples). Such coaxial arrangement of the gripping member or yaw axes may define a common yaw axis. This can allow the protrusion portions 164a,b to be moved between an open configuration in which the protrusions are 164a,b are spaced apart from each other (as shown in FIG. 14) and a closed configuration in which the protrusions 164a,b contact and/or bear against each other (as shown in FIG. 15).

Figure 5:
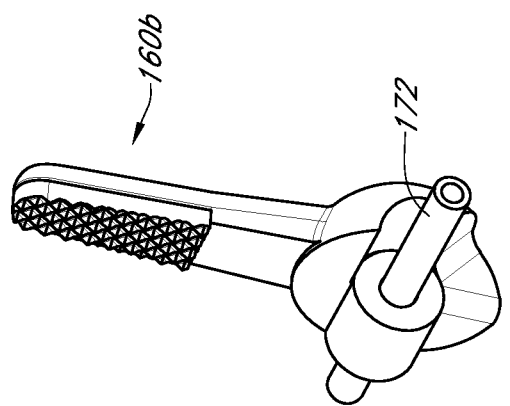
FIG. 5 is a perspective view of a protrusion and base of a tip for a surgical instrument pivotable about a pin.
Figure 8:
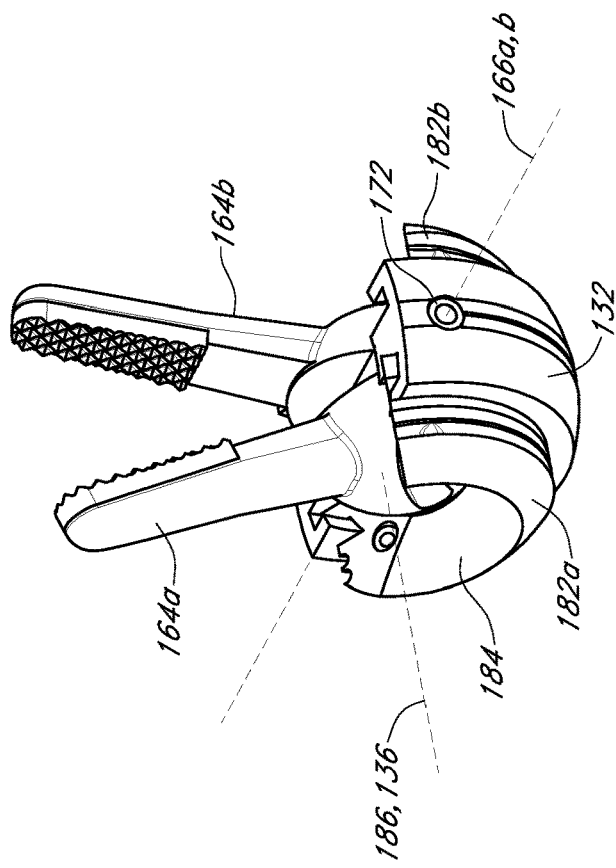
FIG. 8 is a perspective view of a body portion or linkage member combined with the components of FIG. 7.

To help provide this desired range of motion, the bases 162a,b, in this example, are pivotally coupled to the cradle 132 via a common pin joint 170 (as shown in FIG. 7) that utilizes a pin 172 (as shown in FIG. 5) that extends through the bases 162a,b and into corresponding apertures defined by the cradle 132. Preferably, the pin 172 is hollow to accommodate a wire or cable as described herein, but alternative connection mechanisms may be used in other examples.

Figure 16:
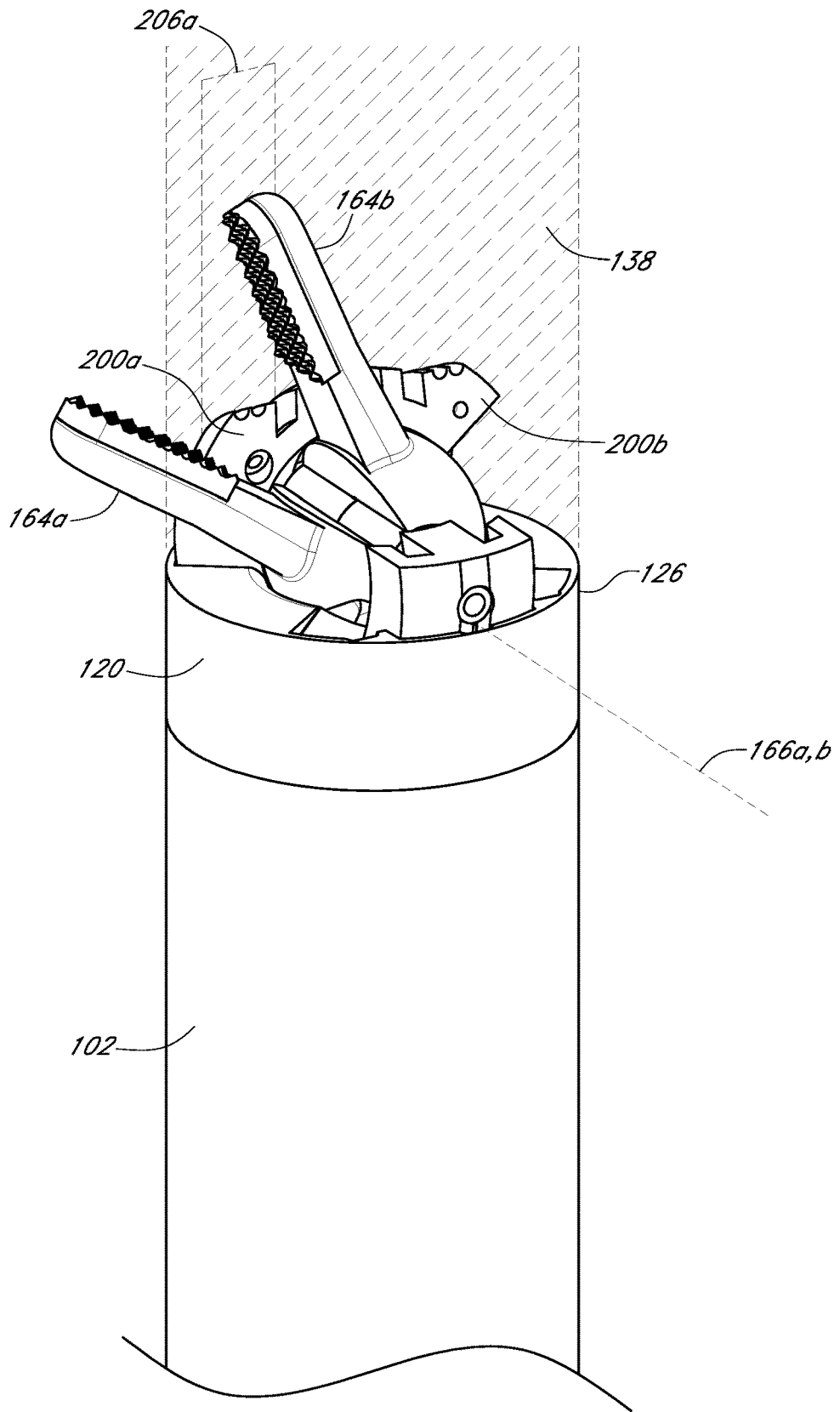
FIG. 16 is a perspective view of the surgical tip of FIG. 1 in a first yaw position.
Figure 17:
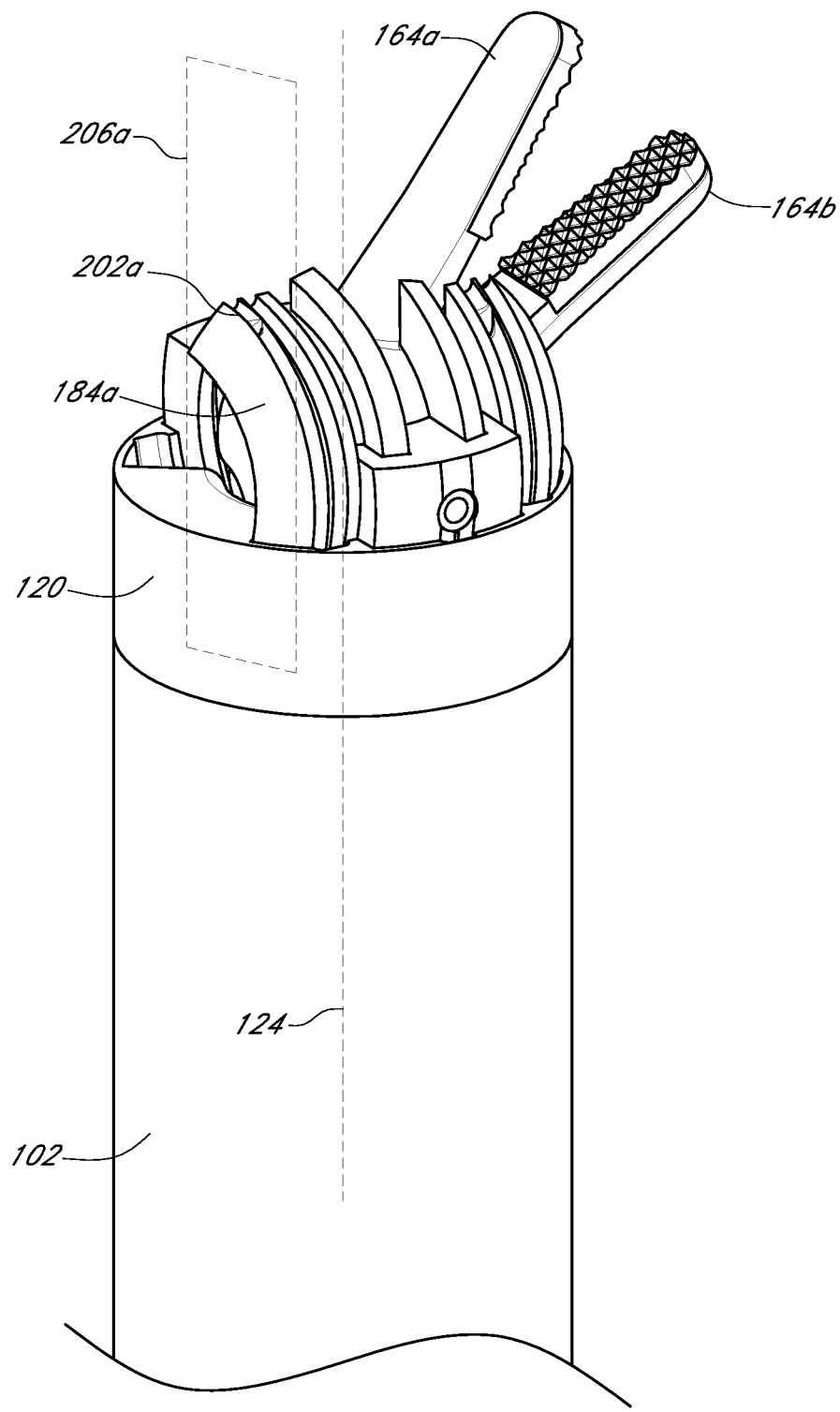
FIG. 17 is a perspective view of the surgical tip of FIG. 1 in a second yaw position.
Figure 19:
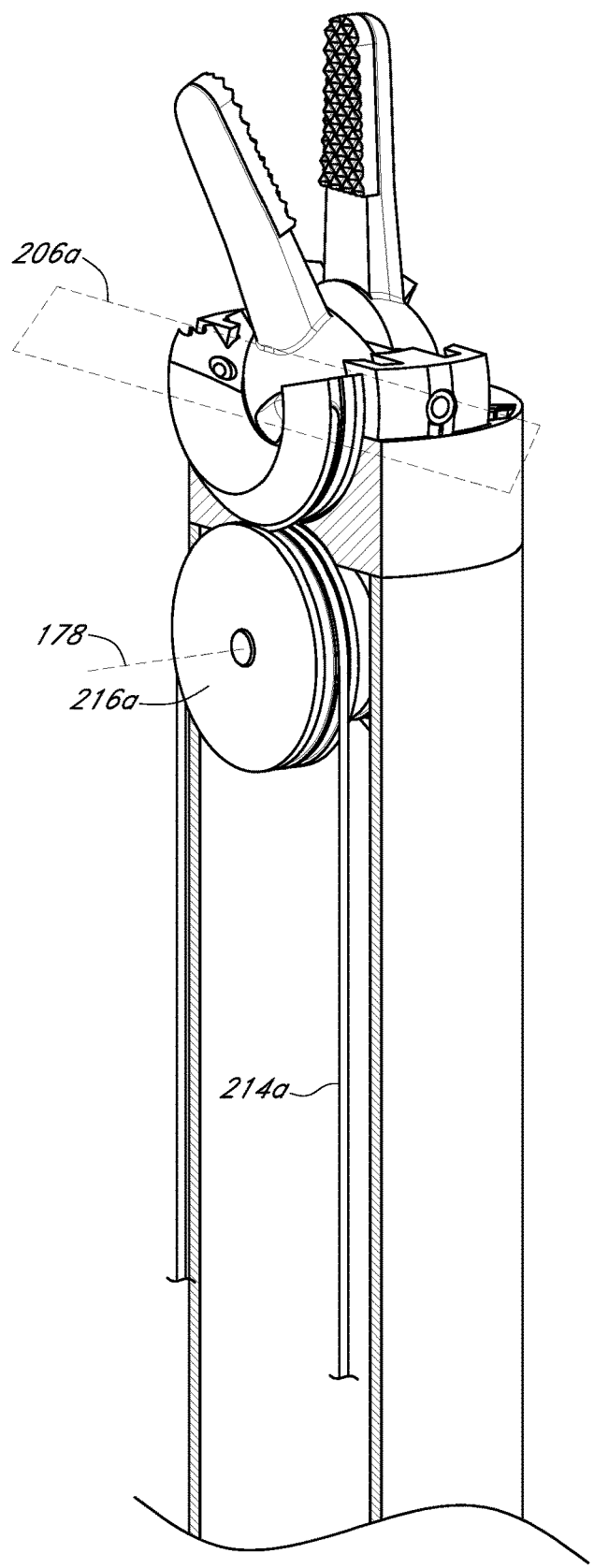
FIG. 19 is a side view of the surgical tip with a portion of the frame and elongate shaft removed and in a first yaw position.
Figure 20:
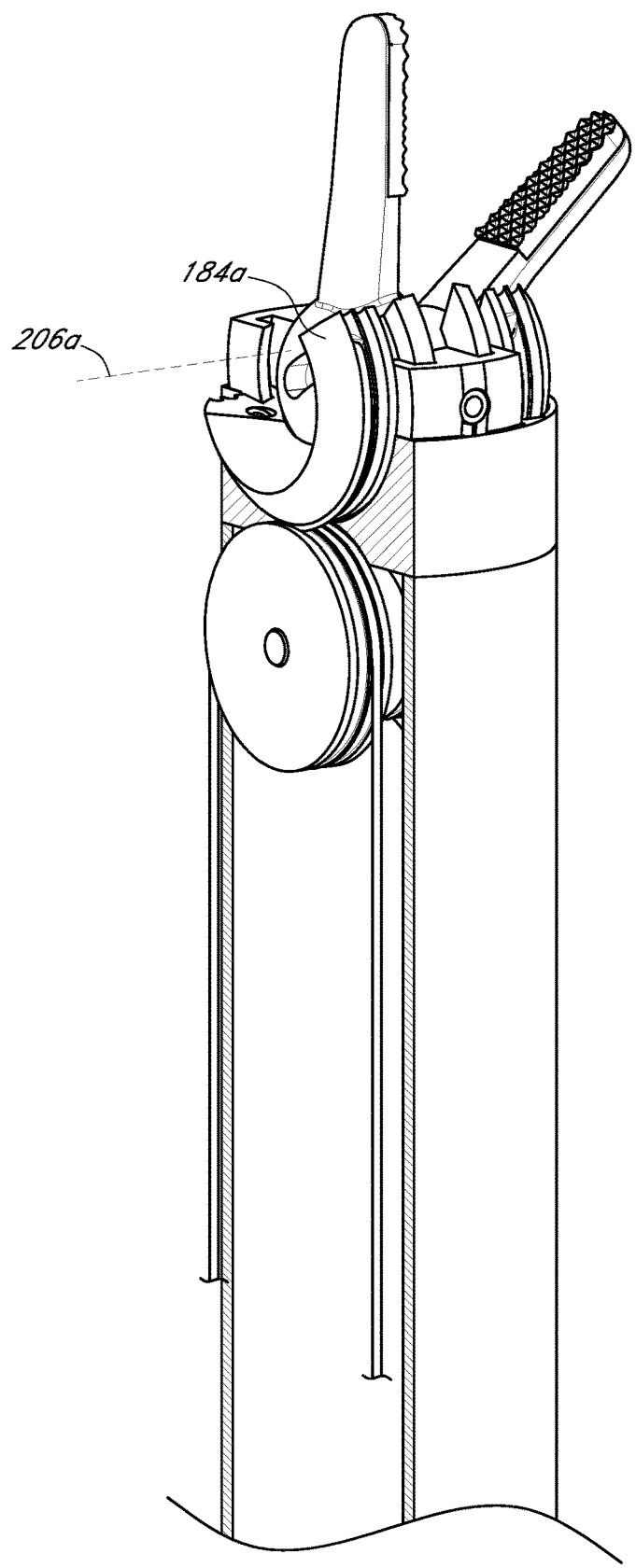
FIG. 20 is a side view of the surgical tip with a portion of the frame and elongate shaft removed and in a second yaw position.

Preferably, the gripping portions 160a,b are moveable about the yaw axes 166a,b independently of each other, for example using a suitable actuating apparatus as described herein (e.g., as shown in FIGS. 19-20). This can help provide both the opening and closing operation of the tip 102 (by moving the gripping portions 160a,b away and toward each other), but can also be used to change the yaw position of the whole grasping assembly by moving both of the gripping portions 160a,b in the same direction as each other. For example, the gripping portions 160a,b are shown in one open position in FIG. 14. If the gripping portions 160a,b are moved toward each other, the grasping assembly can be closed, as shown in FIG. 15. If, alternatively both gripping portions 160a,b are rotated in the same direction as each other, the grasping assembly can be pivoted to the left (as shown in FIG. 16) or right (as shown in FIG. 17) about the yaw axes 166a,b while still remaining open.

Preferably, the gripping portions 160a,b are also moveable about the yaw axes 166a,b independently of the movement of the cradle 132 and regardless of the position of the cradle 132 along its range of motion. This can allow yaw movements of the gripping portions 160a,b to be done independently of the pitch movements of the cradle 132. This may help provide predictable movement of the tip 102.

To help provide the desired range of motion and relatively compact overall size of the tip, the tip 102 is preferably arranged so that the frame axis 124 or shaft axis intersects the pitch axis 136 (as shown in FIG. 7). Optionally, the tip 102 may be configured so that the frame axis or shaft axis also intersects at least one of the first grip axis 166a and the second grip axis 166b, and preferably can intersect both axes 166a,b (as they are coaxial in this example). In one preferred embodiment, as illustrated, all of the axes (i.e., the frame axis 124/shaft axis, the pitch axis 136, the first grip axis 160a and the second grip axis 160b) can all intersect each other at a common intersection point 180, as shown in FIG. 7. The common intersection point 180 is preferably located axially outboard of the outer or distal end 126 of the frame 120 or shaft and within the frame projection area 138.

To help drive the movement of the gripping portions 160a,b, the tip 102 includes an actuating apparatus that is configured to independently rotate the cradle 132 about the pitch axis 136, pivot the first gripping member 160a about the first yaw axis 160a, and pivot the second gripping member 160b about the second yaw axis 160b. A variety of actuating apparatuses may be used, including gears, pulleys, wires, electric motors, pneumatic or hydraulic controls, or the like. Preferably, to help simplify construction and/or reduce overall size and weight, and/or to help improve robustness, the actuating apparatus can be a manual apparatus that does not require the use of electronics or motors within the tip 102 itself.

Referring also to FIGS. 4, 9 and 18-20, in the present example the actuating apparatus can include a cradle cable 174 that extends axially through the frame 120 and shaft 102 and is connectable to the drive apparatus 108. The cradle cable 174 is connected to the cradle 132, via extending through the hollow interior defined by the pin 172 whereby movement of the cradle cable 174 through the frame 120 or shaft causes rotation of the cradle 132 about the pitch axis 136. In this arrangement, the cradle cable 174 may pass through the hollow pivot pin 172 and a portion of the cradle cable 174 within the hollow pivot pin may extend along the first yaw axis 166a, which may help reduce the overall size of the tip and may help secure the cable 174.

Figure 9:
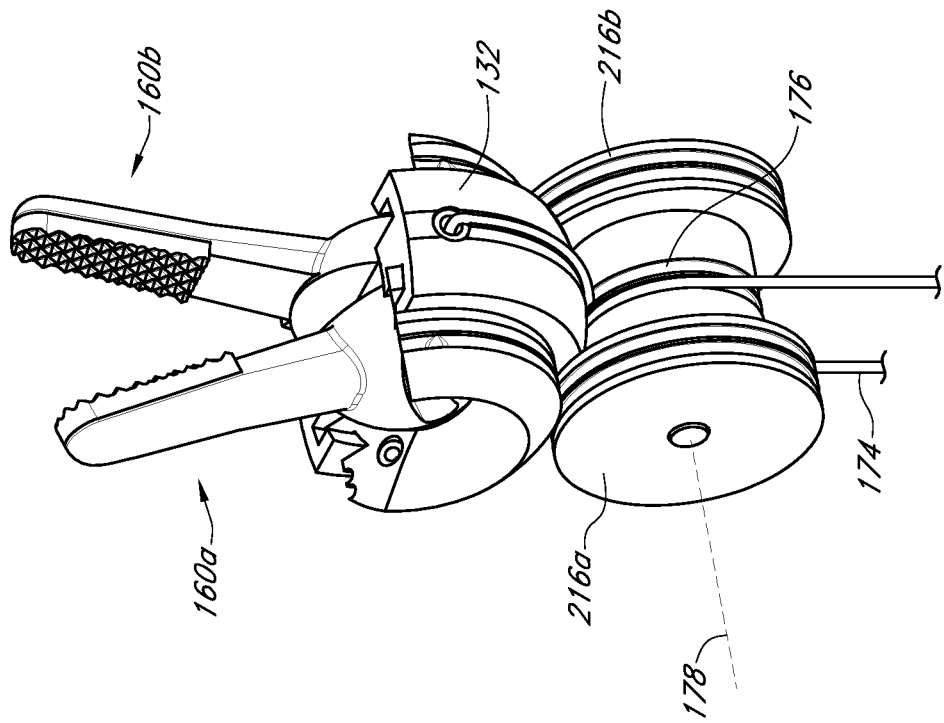
FIG. 9 is a perspective view of a cradle pully system combined with the components of FIG. 8.

Preferably, the actuating apparatus can also include one or more pulleys to help guide any cables or other members used to help actuate the tip 102. In this example, as shown in FIG. 9, the actuating apparatus includes a suitable cradle pulley, such as pulley 176 that is disposed axially inboard from the outer or distal end 126 of the frame 120 or shaft and is rotatable about a cradle pulley axis 178 that is substantially parallel to the pitch axis 136 and orthogonal to the frame axis 124 or shaft axis. The cradle pulley 176, in this example, is flanked by respective cable pulleys 216a,b (see FIGS. 9 and 11) that are separately rotatable, and are described in more detail herein. The cradle pulley 176 is preferably configured to help guide the cradle cable 174 and to help keep the cradle cable 174 in close proximity to the curved outer surface of the cradle 132. This can also help keep portions of the cable 174 that are downstream from the pulley 176 in the substantially same lateral position and can help translate the generally axial pulling on the cable 176 into the desired rotating motion of the cradle 132.

To help drive the gripping members 160a,b, the actuating apparatus may include any suitable type of linking or driving member that is connected to the gripping members 160a,b. In the illustrated example, each gripping member 160a,b is driven by a corresponding linkage member 182a,b, which are substantially identical in this example but may have different configurations in other examples. For clarity, one linkage member and its operation are described in detail below, but the second linkage member can include analogous features and operate in an analogous manner.

Referring to FIG. 8-11, in this example the linkage members are provided in the form of generally curved or arcuate or linkage members 182a,b that have a curved body portion 184 that is configured to be rotatable about a respective drive axis 186 which, in this example, is coaxial with the pitch axis 136 but, in other examples, may be parallel to but offset from the pitch axis 136. The body portion 184 is configured to be movable relative to the frame 120 or shaft about the drive axis 186 independently of the cradle 132 and the opposite or second body portion 184. The body portions 184 are drivingly connect to the respective gripping portions 160a,b such that rotation of the body portions 184 about the drive/pitch axis 186, 136 will cause pivoting of the gripping portions 160a,b about the yaw axes 166a,b. This can help provide the independent movement of the first gripping portions 160a,b.

In the illustrated example, as shown in FIGS. 11-12, this driving connection is achieved by utilizing a pin 188a,b projecting from each body portion 184a,b, respectively, that is slidably received within a slot 190a,b (e.g., may be non-linear), respectively, on the base 162a,b of the respective gripping portion 160a,b. The slots 190a,b are shaped and configured so that contact between the respective pin 188 and the slot 190 as the pin 188 moves with the body portions 184 about the pitch axis 136 causes the corresponding pivoting of the base portions 162a,b about the yaw axis 166a,b. While shown with a pin 188 on the body portion 184 and slot 190 on the bases 162a,b, the arrangement of these features may be reversed or other suitable engagement mechanisms may be used, as described elsewhere herein.

To help provide a compact overall design, the body portions 184a,b are configured to be coupled to and at least partially supported by the cradle 132, and may utilize any suitable connection mechanism. In the illustrated example, the body portions 184a,b each include a respective arcuate rib/rail 196a,b that is slidably received within a respective arcuate slot 198a,b on the cradle 132 (although these features may be reversed/swapped in other examples (e.g., such that the rib/rail is provided on the cradle 132 and slides within a slot on the body portions 184). Rib/rail 196a,b may movably mount body portions 184a,b on the respective cradle 132a,b and at least partially support the body portions 184a,b on the respective cradle 132a,b.

Like cradle 132, each body portion 184a,b may extend between respective ends 200a,b and 202a,b by a respective linkage or body portion angle 204 (shown as arrow 204 in FIG. 11) that may be between about 45 degrees and about 270 degrees, and preferably is about 180 degrees and may optionally be generally the same or substantially the same as the cradle angle 146.

Also like cradle 132, each body portion 184a,b can be positionable in a home/neutral position in which the first body portion end 200a,b and the second body portion end 202a,b are each disposed axially outboard of the outer or distal frame end or distal shaft end, as shown in FIG. 14. When in this position, respective body portion planes (only one plane 206a is shown in FIGS. 14, 16 and 17 for clarity) are generally orthogonal to the frame axis 124 or shaft axis. Each body portion 184a,b is then rotatable relative to the frame 120, and independently of the cradle 132 in the first direction from its home/neutral position to a first body portion limit position (through one or more intermediate positions), in which the first body portion end 200a is disposed axially outboard of the outer or distal frame end 126 or distal end of the shaft and the second body portion end 202a is disposed axially inboard of the outer or distal frame end 126, as shown in FIG. 16. One of skill in the art will appreciate that while a neutral position and a first body portion limit position are described, there may exist an infinite number of positions between the neutral position and the first body portion limit position, for example intermediate positions. When the body portion 184a is in its first body portion limit position; i) the body portion plane 206a is substantially parallel to the frame axis 124 (as shown in FIG. 16), and ii) the member or protrusion 164a is spaced from the frame axis 124 or shaft axis and extends laterally beyond the edge of the frame 120 (e.g., outside the frame projection area 138). A similar configuration can be achieved with the other body portion 184b and member or protrusion 164b, as shown in FIG. 17.

Each body portion 184a,b is also rotatable relative to the frame 120, and independently of the cradle 132 in the opposing second direction from the home/neutral position to a second body portion limit position (through any one or more intermediate positions), in which the second body portion end 202a is disposed axially outboard of the outer or distal frame end 126 or shaft distal end and the first body portion end 200a is disposed axially inboard of the outer or distal frame end 126 (as shown in FIG. 17). When the body portion 184a is in the second body portion limit position: i) the first body portion plane 206a is substantially parallel to the frame axis 124 or shaft axis, and ii) the first protrusion 164a is intersected by the frame axis 124 or shaft axis, as shown in FIG. 17. One of skill in the art will appreciate that while a neutral position and a second body portion limit position are described, there may exist an infinite number of positions between the neutral position and the second body portion limit position, for example intermediate positions.

Figure 13:
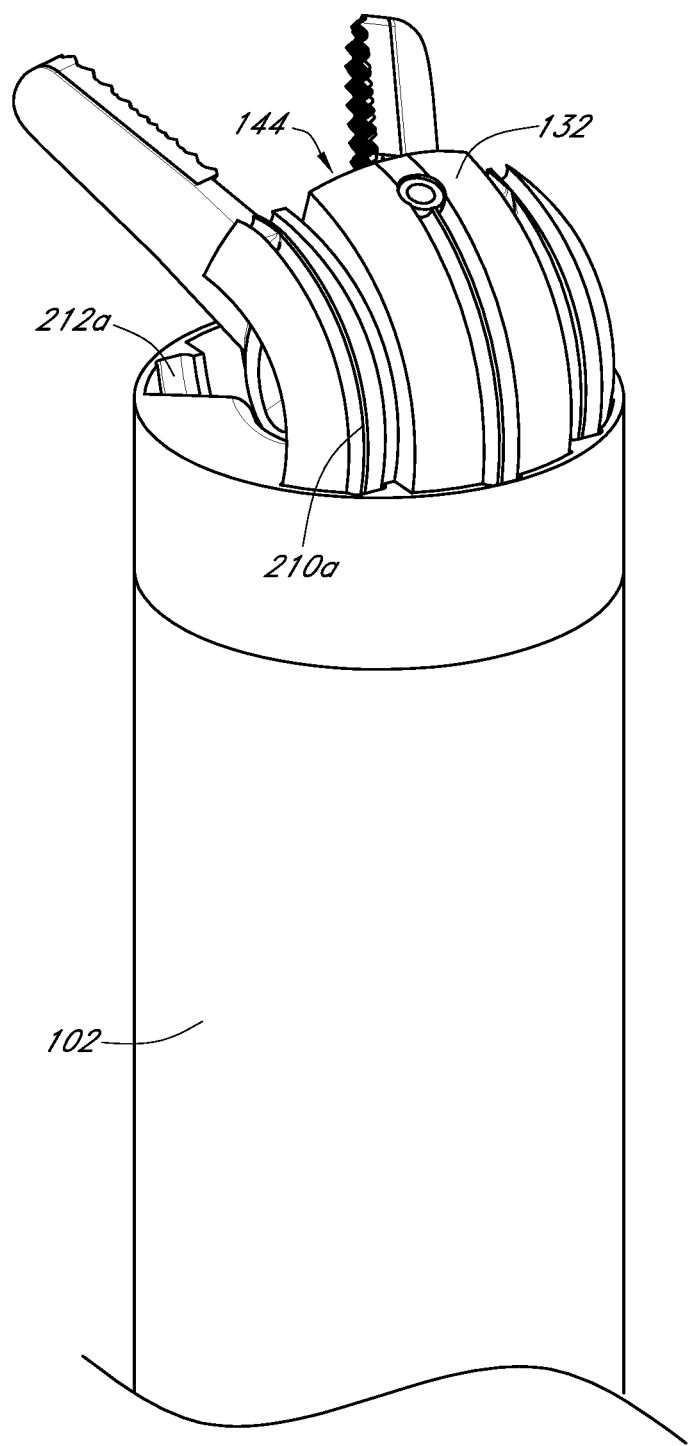
FIG. 13 is a perspective view of the surgical tip of FIG. 1 in a second pitch position.

As the body portions 184a,b can move and be driven independently of the cradle 132, the cradle 132 can, in this example, be movable between its first limit position and the second limit position while the first arcuate body portion is in the first body portion limit position and while the first arcuate body portion is in the second body portion limit position and in other positions therebetween (see FIGS. 12 and 13).

Preferably, to help reduce the overall size of the tip, the body portions 184a,b are configured, as shown in the present example, so that they are disposed within the frame projection area 138 (i.e., the axial projection of the cross-sectional area of the frame 120) when in their respective home/neutral position, first body portion limit position, and second body portion limit position.

If additional stability is desired, in addition to being guided and supported by the cradle 132, each body portion 184a,b can include a respective arcuate frame rail portion 210a,b that slidingly engages with a respective and complementary link groove or bushing 212a,b on the frame.

The body portions 184a,b can be driven using any suitable mechanism, and in this example are drive by link cables, such as cable 214a shown in FIGS. 18-20, that are connected to the body portions 184a,b and can be guided by corresponding link pulleys, such as pulley 216a that are rotatable relative to the frame 120 or shaft. In this example, the cable pulley 216a is configured to be adjacent to the cradle pulley 176, as shown in FIG. 11, such that cable pulley 216a also rotates about the common pulley axis 178, but in other examples the cable pulley 216a may be in a different location or may have a different arrangement.

The cables 174 and 214a,b can extend through the interior of the shaft 102 to the drive apparatus 108 and can be engaged by respective capstans 220 that can pull on the cables 174 and 214 independently from each other, to independently drive the movements of the cradle 132, body portions 184a,b, and associated gripping portions 160a,b.

The systems and methods of the various embodiments and variations thereof can be embodied and/or implemented at least in part as a machine configured to receive a computer-readable medium storing computer-readable instructions. The instructions are preferably executed by computer-executable components preferably integrated with the system and one or more portions of the processor communicatively coupled to an actuating apparatus and/or computing device. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions.

As used in the description and claims, the singular form "a", "an" and "the" include both singular and plural references unless the context clearly dictates otherwise. For example, the term "limit" may include, and is contemplated to include, a plurality of limits. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 10%, 5%, 1% or 0.1%. All numerical ranges provided herein are inclusive of the stated start and end numbers. The term "substantially" indicates mostly (i.e., greater than 50%) or essentially all of a device, substance, or composition. For the lengths and widths described herein about may, in some examples, mean plus or minus 10% of the stated value but is not limited to exactly 10% or less in all situations.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The invention claimed is:

1. A tip for a surgical instrument, the tip comprising:
a cradle that is moveably mounted to a distal end of an elongate shaft and configured to rotate relative to the elongate shaft about a pitch axis substantially orthogonal to a shaft axis of the elongate shaft; and
a member pivotally coupled to the cradle and configured to move with the cradle about the pitch axis and to pivot relative to the cradle about a first grip axis,
wherein the first grip axis and the pitch axis are substantially orthogonal and intersect at a common intersection point, and
wherein the member is positionally controlled such that movement about the pitch axis and pivoting about the first grip axis is about the common intersection point.

2. The tip of claim 1, wherein the member is movable toward and away from a shaft axis of the elongate shaft about a yaw axis.

3. The tip of claim 2, further comprising a second member pivotally coupled to the cradle and configured to move with the cradle about the pitch axis and to pivot relative to the cradle about a second grip axis that is substantially orthogonal to the pitch axis, wherein the second member is movable relative to both the cradle and the member about the yaw axis.

4. The tip of claim 3, wherein the member and the second member are selectably movable toward and away from each other between a closed configuration in which the member contacts the second member and an open configuration in which the member is spaced apart from the second member.

5. The tip of claim 3, wherein the first grip axis and the second grip axis are coaxial with each other.

6. The tip of claim 3, wherein the member comprises a first base and the second member comprises a second base that are connected to the cradle via a common pin joint.

7. The tip of claim 6, wherein the member or the first base and the second member or the second base are pivotally connected to the cradle using a hollow pivot pin such that a cradle cable is configured to pass through the hollow pivot pin.

8. The tip of claim 7, wherein a portion of the cradle cable within the hollow pivot pin is configured to extend along the first grip axis.

9. The tip of claim 3, further comprising an actuating apparatus that is configured to independently rotate the cradle about the pitch axis, pivot the member about the first grip axis, and pivot the second member about the second grip axis.

10. The tip of claim 9, wherein the actuating apparatus comprises a cradle cable extending axially through the elongate shaft and being connectable to a cradle drive apparatus, the cradle cable being connected to the cradle whereby movement of the cradle cable through the elongate shaft causes rotation of the cradle about the pitch axis.

11. The tip of claim 3, further comprising a first linkage member having a first arcuate body portion that is rotatable about the pitch axis, relative to the elongate shaft, and independently of the cradle, and a second linkage member having a second arcuate body portion that is rotatable about the pitch axis, relative to the elongate shaft, and independently of both the cradle and the first arcuate body portion.

12. The tip of claim 11, wherein the first linkage member is drivingly connected to the member so that pivoting of the first arcuate body portion about the pitch axis causes a corresponding pivoting of the member about the first grip axis, and wherein the second linkage member is drivingly connected to the second member so that pivoting of the second arcuate body portion about the pitch axis causes a corresponding pivoting of the second member about the second grip axis.

13. The tip of claim 1, further comprising an actuating apparatus that is configured to independently rotate the cradle about the pitch axis, and pivot the member about the first grip axis.

14. The tip of claim 1, wherein the member is one of: an end-effector, a grasper, a sensorized end-effector, a force-torque sensor, a material removal tool, a collision sensor, a tool changer, a laser, a hook, a cautery/electrosurgery tip, a clip applier, a needle driver, a scissors, an ultrasonic energy instrument, an irrigation tip, a vessel sealer, a stapler, a base, a protrusion, or a base coupled to a protrusion.

15. The tip of claim 1, wherein the cradle comprises an arcuate body and a rail portion that is configured to slidingly engage with a first complementary bushing structure on the elongate shaft, and wherein the elongate shaft comprises a second complementary bushing structure that is configured to slidingly engage the rail portion of the cradle, and wherein the second complementary bushing structure is spaced apart from the first complementary bushing structure.

16. The tip of claim 15, wherein the arcuate body of the cradle extends between a first cradle end and a second cradle end and defines a cradle angle that is between about 45 degrees and about 270 degrees.

17. The tip of claim 15, wherein the elongate shaft further comprises a frame, such that one or more of: the first complementary bushing structure, the second complementary bushing structure, or a cradle cable are positioned in the frame.

18. A method of manipulating a tip of a surgical instrument, the method comprising: rotating a first end-effector, pivotally coupled to a cradle that is moveably mounted to a distal end of an elongate shaft, about a pitch axis about which the cradle is configured to rotate and a first grip axis that is substantially orthogonal to the pitch axis; and rotating a second end-effector pivotally coupled to the cradle about the pitch axis and a second grip axis that is substantially orthogonal to the pitch axis, wherein: the second end-effector is rotatable about the second grip axis independently of the rotation of the first end-effector about the first grip axis, coordinated rotation of the first end-effector about the first grip axis and the second end-effector about the second grip axis causes the first end-effector and the second end-effector to move toward and away from each other between a closed configuration in which the first end-effector contacts the second end-effector and an open configuration in which the first end-effector is spaced apart from the second end-effector, the pitch axis that is substantially orthogonal to a shaft axis of the elongate shaft, the first grip axis, and the second grip axis intersect at a common intersection point, and the first end-effector is positionally controlled such that movement about the pitch axis and movement about the first grip axis is about the common intersection point.

19. The method of claim 18, wherein the first grip axis and second grip axis are coaxial with each other and define a common yaw axis.

20. The method of claim 18, wherein the second end-effector is rotatable about the pitch axis independently of the rotation of the first end-effector about the pitch axis.

21. A tip for a surgical instrument, the tip comprising:
   a cradle moveably mounted to a distal end of an elongate shaft and configured to rotate relative to the elongate shaft about a pitch axis substantially orthogonal to a shaft axis of the elongate shaft, the cradle comprising:
      an arcuate body, and
      a rail portion that is configured to slidingly engage with a first complementary bushing structure and a second complementary bushing structure on the elongate shaft, the second complementary bushing structure being spaced apart from the first complementary bushing structure; and
   a member pivotally coupled to the cradle and configured to move with the cradle about the pitch axis and to pivot relative to the cradle about a first grip axis, wherein:
   the member is positionally controlled such that movement about the pitch axis and pivoting about the first grip axis is about a common intersection point, and
   the first grip axis and the pitch axis are substantially orthogonal and intersect at the common intersection point.

* * * * *